(12) United States Patent
Millar

(10) Patent No.: US 7,799,525 B2
(45) Date of Patent: Sep. 21, 2010

(54) METHODS FOR GENOME AMPLIFICATION

(75) Inventor: Douglas Spencer Millar, Revesby (AU)

(73) Assignee: Human Genetic Signatures Pty Ltd., North Ryde, NSW (AU)

( * ) Notice: Subject to any disclaimer, the term of this patent is extended or adjusted under 35 U.S.C. 154(b) by 786 days.

(21) Appl. No.: 10/561,029

(22) PCT Filed: May 31, 2004

(86) PCT No.: PCT/AU2004/000722

§ 371 (c)(1),
(2), (4) Date: Mar. 16, 2007

(87) PCT Pub. No.: WO2004/111266

PCT Pub. Date: Dec. 23, 2004

(65) Prior Publication Data

US 2007/0178457 A1 Aug. 2, 2007

(30) Foreign Application Priority Data

Jun. 17, 2003 (AU) ............................. 2003903034
Jun. 17, 2003 (AU) ............................. 2003903039

(51) Int. Cl.
*C12Q 1/68* (2006.01)
*C12P 19/34* (2006.01)

(52) U.S. Cl. ......................................... 435/6; 435/91.2

(58) Field of Classification Search ................. None
See application file for complete search history.

(56) References Cited

U.S. PATENT DOCUMENTS

| | | | |
|---|---|---|---|
| 5,629,156 A | 5/1997 | Shah et al. | |
| 5,750,338 A | 5/1998 | Collins et al. | |
| 5,786,146 A | 7/1998 | Herman et al. | |
| 5,824,517 A | 10/1998 | Cleuziat et al. | |
| 5,952,174 A | 9/1999 | Nikiforov et al. | |
| 6,156,501 A | 12/2000 | McGall et al. | |
| 6,265,171 B1 | 7/2001 | Herman et al. | |
| 6,331,393 B1 | 12/2001 | Laird et al. | |
| 6,692,918 B2 | 2/2004 | Kurn | |
| 6,960,436 B2 | 11/2005 | Cottrell | |
| 7,008,770 B1 * | 3/2006 | Berlin ............................. | 435/6 |
| 7,288,373 B2 | 10/2007 | Millar et al. | |
| 7,504,207 B2 | 3/2009 | Bergquist | |
| 2002/0086324 A1 | 7/2002 | Laird et al. | |
| 2002/0142397 A1 | 10/2002 | Collas et al. | |
| 2003/0073081 A1 | 4/2003 | Mukai et al. | |
| 2003/0119025 A1 | 6/2003 | Olek et al. | |
| 2003/0143577 A1 * | 7/2003 | Hogrefe et al. ............... | 435/6 |
| 2004/0086944 A1 | 5/2004 | Grigg et al. | |
| 2004/0203004 A1 | 10/2004 | Bernard et al. | |
| 2004/0219539 A1 | 11/2004 | Millar et al. | |
| 2005/0019762 A1 | 1/2005 | Olek | |
| 2005/0059003 A1 | 3/2005 | Enoki et al. | |
| 2005/0118578 A1 | 6/2005 | Mineno et al. | |
| 2005/0202490 A1 | 9/2005 | Makarov | |
| 2006/0014144 A1 * | 1/2006 | Christensen et al. ............ | 435/6 |
| 2006/0051771 A1 | 3/2006 | Murphy et al. | |
| 2006/0166203 A1 | 7/2006 | Took | |
| 2007/0020633 A1 | 1/2007 | Millar | |
| 2007/0042365 A1 | 2/2007 | Millar et al. | |
| 2007/0178459 A1 | 8/2007 | Millar | |
| 2007/0190530 A1 | 8/2007 | Birkner et al. | |
| 2007/0264653 A1 | 11/2007 | Berlin et al. | |
| 2008/0050738 A1 | 2/2008 | Millar | |
| 2009/0029346 A1 | 1/2009 | Millar et al. | |
| 2009/0130657 A1 | 5/2009 | Millar | |
| 2009/0263909 A1 | 10/2009 | Millar | |

FOREIGN PATENT DOCUMENTS

| | | |
|---|---|---|
| DE | 103 31 107 B3 | 12/2004 |
| EP | 1 130 113 | 9/2001 |
| EP | 1 319 718 | 6/2003 |
| WO | WO 95/01456 | 1/1995 |
| WO | WO 95/22623 | 8/1995 |
| WO | WO 97/41254 | 11/1997 |
| WO | WO 97/45559 | 12/1997 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 03/008623 A2 | 1/2003 |
| WO | WO 03/048732 | 6/2003 |

(Continued)

OTHER PUBLICATIONS

Dean et al. "Comprehensive human genome amplification using multiple displacement amplification." *PNAS*; 99(8):5261-5266 (2002).

(Continued)

*Primary Examiner*—Kenneth R. Horlick
*Assistant Examiner*—David C Thomas
(74) *Attorney, Agent, or Firm*—Knobbe Martens Olson & Bear LLP

(57) ABSTRACT

A method for whole genome amplification comprising (a) treating genomic DNA with a modifying agent which modifies cytosine bases but does not modify 5'-methyl-cytosine bases under conditions to form single stranded modified DNA; (b) providing a population of random X-mers of exonuclease-resistant primers capable of binding to at least one strand of the modified DNA, wherein X is an integer 3 or greater; (c) providing polymerase capable of amplifying double stranded DNA, together with nucleotides and optionally any suitable buffers or diluents to the modified DNA; and (d) allowing the polymerase to amplify the modified DNA.

22 Claims, 3 Drawing Sheets

FOREIGN PATENT DOCUMENTS

| | | |
|---|---|---|
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004/065625 | 8/2004 |
| WO | WO 2004/090166 | 10/2004 |
| WO | WO 2004/096825 | 11/2004 |
| WO | WO 2004/111266 | 12/2004 |
| WO | WO 2005/021778 | 3/2005 |
| WO | WO 2005/056790 A1 | 6/2005 |
| WO | WO 2006/058393 | 6/2006 |

OTHER PUBLICATIONS

Grigoriev et al. "A Triple Helix-forming Oligonucleotide-Intercalator Conjugate Acts as a Transcriptional Repressor via Inhibition of NF κB Binding to Interleukin-2 Receptor α-Regulatory Sequence." *The Journal of Biological Chemistry*; 267(5):3389-3395 (1992).

Grunau et al. "Bisulfate genomic sequencing: systematic investigation of critical experimental parameters." *Nucleic Acids Research*; 29(13):1-7 (2001).

Hosono et al. "Unbiased Whole-Genome Amplification Directly from Clinical Samples." *Genome Research*; 13:954-964 (2003).

Sakaguchi et al. "Cautionary Note on the Use of dUMP-Containing PCR Primers with *Pfu* and Vent$_R$® DNA Polymerases." *Biotechniques*; 21(3):368 & 370 (1996).

Telenius et al. "Degenerate Oligonucleotide-Primed PCR: General Amplification of Target DNA by a Single Degenerate Primer." *Genomics*; 13(3):718-725 (1992).

Christensen et al., "Intercalating nucleic acids containing insertions of 1-o-(1-pyrenylmethyl)glycerol: stabilization of dsDNA and discrimination of DNA over RNA." Nucleic Acid Res. vol. 30, No. 22, pp. 4918-4925, (2002).

Clark et al., "High sensitivity mapping of methylated cytosines." Nucleic Acids Research, 22(15): 2990-2997 (1994).

Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.

www.ncbi.nlm.nih.gov Database Accession No. M24485.

Eads et al., "MethylLight: a high-throughput assay to measure DNA methylation." Nucleic Acids Research, 28(8):e32, i-viii (2000).

Feil, et al., "Methylation analysis on individual chromosomes: improved protocol for bisulphite genomic sequencing." (1994) Nucleic Acids Research 22(4): 695-696.

Frommer et al., "A genomic sequencing protocol that yields a positive display of 5-methylcytosine residues in individual DNA strands," Proc. Natl. Acad. Sci. 89: 1827-1831 (1992).

Hakelien et al., "Reprogramming fibroblasts to express T-cell functions using cell extracts." Nature Briotechnology, 20(5): 460-466 (2002).

Hakelien et al., "Novel Approaches to transdifferentiation" Cloning and Stem Cells, 4: 379-387 (2002).

Herman, et al., "Methylation-specific PCR: a novel PCR assay for methylation status of CpG islands." (1996) Proc. Natl. Acad. Sci. U.S.A. 93:9821-9826.

International Human Genome Sequencing Consortium, "Initial sequencing and analysis of the human genome," Nature, 409(6822): 860-921 (2001).

International Preliminary Report on Patentability issued on the corresponding PCT Application No. PCT/AU2006/000698, dated Apr. 20, 2007.

International Search Report Issued on the corresponding PCT Application No. PCT/AU2006/000698, dated Aug. 1, 2006.

Kinoshita et al., "Methylation of the androgen receptor minimal promoter silences transcription in human prostate cancer." Cancer Research, 60(13): 3623-3630 (Jul. 1, 2000).

Kono, "Nuclear transfer and reprogramming." Reviews of Reproduction, vol. 2 No. 2, pp. 74-80 (May 1997).

Millar et al., "A distinct sequence (ATAAA)$_n$ separates methylated and unmethylated domains at the 5'-end of the GSTP1 CpG island," J. Biol. Chem., 275(32): 24893-24899 (2000).

Millar et al., "Detailed methylation analysis of the glutathione S-transferase pi (GSTPI) gene in prostate cancer," Oncogene 18(6): 1313-1324 (1999).

Monk, "Epigentic programming of differential gene expression in development and evolution" Dev. Genetics, vol. 17, pp. 188-197 (1995).

Newton et al., "The production of PCR products with 5' single-stranded tails using primers that incorporate novel phosphoramidite intermediates." Nucleic Acid Res. vol. 21 No. 5, pp. 1155-1162 (1993).

Nilsson et al., "Padlock Probes: Circularizing Oligonucleotides for localized DNA detection", Science; 265:2085-2088 (1994).

Office Action in U.S. Appl. No. 10/416,637 dated May 4, 2006.
Office Action in U.S. Appl. No. 10/428,310 dated Aug. 31, 2006.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Nov. 3, 2006.
Office Action in U.S. Appl. No. 10/536,633 dated Apr. 4, 2007.
Office Action in U.S. Appl. No. 10/536,633 dated Jan. 25, 2007.

Okada, et al., "Sequence Determination of Rat U5 RNA Using a Chemical Modification Procedure for Counteracting Sequence Compression." (1982) J. Biochem. 91: 1281-1291.

Olek, et al. "A modified and improved method for bisulphite based cytosine methylation analysis." (1996) Nucleic Acids Research, 24(24): 5064-5066.

Paulin et al., "Urea improves efficiency of bisulphite-mediated sequencing of 5'-methylcytosine in genomic DNA." Nucleic Acid Research, 26(21): 5009-5010 (Nov. 1, 1998).

Pietrobono et al., "Quantitative analysis of DNA demethylation and transcriptional reactivation of the FMR1 gene in fragile X cells treated with 5-azadeoxycytidine." Nucleic Acids Research, 30(14): 3278-3285 (2002).

Raizis et al., "A Bisulfite Method of 5-methylcytosine mapping that minimizes template degradation", Anal. Biochem., 226: 161-166 (1995).

Rein et al., "Identifying 5-methylcytosine and related modifications in DNA genomes." Nucleic Acids Research, 26 (10): 2255-2264 (1998).

Robertson et al., "Blood" 90: 4480-4484 (1997).

Robertson et al. "DNA methylation: past, present, and future directions." Carcinogenesis. 21(3): 461-467 (2000).

Sakashita et al., "Dynamic DNA methylation change in the CpG island region of p15 during human myeloid development," J. Clin. Invest., 108: 1195-1204 (2001).

Shapiro et al., "Deamination of cytosine derivatives by bisulfite. Mechanism of the reaction," J. Am. Chem. Soc., 96: 906-912 (1974).

Specification and Preliminary Amendment from co-pending U.S. Appl. No. 10/555,465, filed Aug. 28, 2006.

Tada et al., "Embryonic germ cells induce epigenetic reprogramming of somatic nucleus in hybrid cells." The EMBO Journal, 16(21): 6510-6520 (1997).

Tohgi et al., "Decrease with age in methylcytosines in the Prometer region of receptor for advanced glycated end products (RAGE) gene in autopsy human cortex", Molecular Brain Research, 65:124-128 (1999).

Venter et al., "The sequence of the human genome," Science, 291 (5523): 1304-1351.

Warnecke et al., "Detection and measurement of PCR bias in quantitative methylation analysis of bisulphite-treated DNA," Nucleic Acids Research, vol. 25 No. 21, pp. 4422-4426, (1997).

Xiong et al., "COBRA: a sensititive and quantitative DNA methylation assay." (1997) Nucleic Acids Research, 25 (12): 2532-2534.

Badal Sushma et al: "The human papillomavirus-18 genome is efficiently targeted by cellular DNA methylation" Virology, vol. 324, No. 2, Jul. 1, 2004, pp. 483-492.

Badal V. et al: "CpG methylation of human papillomavirus type 16 DNA in cervical cancer cell lines and in clinical specimens: Genomic hypomethylation correlates with carcinogenic progression" Journal of Virology, The American Society for Microbiology, US, vol. 77, No. 11, Jun. 1, 2003, pp. 6227-6234.

Baleriola C et al.: "Comparison of a novel HPV test with the Hybrid Capture II (hcII) and a reference PCR method shows high specificity and positive predictive value for 13 high-risk human papillomavirus infections" Journal Of Clinical Virology, Elsevier, Amsterdam, NL, vol. 42, No. 1, May 1, 2008, pp. 22-26.

Extended European Search Report issued in corresponding European Application No. 05821631.8, dated Nov. 7, 2008.

Feng et al: "Detection of hypermethylated genes in women with and without cervical neoplasia." Journal of the National Cancer Institute Feb. 16, 2005, vol. 97, No. 4, Feb. 16, 2005, pp. 273-282.

Gu W. et al, Depletion of *Saccharomyces cerevisiae* tRNAHis Guanylyltransferase Thglp leads to uncharged tRNAH is with additional m5C, Mol Cell Biol. Sep. 2005; vol. 25, No. 18, pp. 8191-8201.

International Search Report issued in corresponding PCT Application No. PCT/AU2006/000755, dated Aug. 30, 2006.

International Search Report issued in corresponding PCT application No. PCT/AU2004/000083, mailed Feb. 24, 2004.

International Search Report issued in corresponding PCT application No. PCT/AU2004/000549, mailed Jul. 23, 2004.

International Search Report issued in corresponding PCT application No. PCT/AU2004/000722, mailed Jun. 29, 2004.

International Search Report issued in corresponding PCT application No. PCT/AU2004/001196, mailed Sep. 27, 2004.

International Search Report issued in corresponding PCT application No. PCT/AU2005/001374, mailed Nov. 9, 2005.

International Search Report issued on corresponding PCT Application No. PCT/AU2008/000367, dated May 14, 2008.

Kalantari, Mina et al. "Conserved methylation patterns of human papillomavirus type 16 DNA in asymptomatic infection and cervical neoplasia," Journal of Virology, vol. 78, No. 23, Dec. 2004, pp. 12762-12772.

Kim T Y et al: "DNA hypermethylation in gastric cancer" Alimentary Pharmacology & Therapeutics, vol. 20, No. Suppl. 1, Jul. 2004, pp. 131-142.

Kozak et al.: "Influence of secondary structure on binding and migration of 40S ribosomal subunits," Cell, vol. 19, 1980, pp. 79-90.

Malyukova A V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Narayan, Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Office Action in U.S. Appl. No. 10/543,017 dated Aug. 8, 2007.
Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 10/570,715 dated Dec. 14, 2009.
Office Action in U.S. Appl. No. 11/573,873 dated May 4, 2009.
Office Action in U.S. Appl. No. 11/573,873 dated Sep. 2, 2009.
Office Action in U.S. Appl. No. 11/660,586 dated Sep. 15, 2009.

Ratushna V.G. et al.: "Secondary structure in the target as a confounding factor in synthetic oligomer microarray design," BMC Genomics, vol. 6, No. 1, Mar. 2005, p. 31.

Supplementary European Search Report issued in corresponding European Application No. 05779000.8, dated Nov. 24, 2008.

Supplementary European Search Report issued on corresponding European Patent Application No. EP 05 81 3335, dated Mar. 12, 2009.

Supplementary European Search Report issued on corresponding European Patent Application No. EP 06 77 4977, dated Jul. 28, 2009.

Ushijima Toshikazu et al: "Aberrant methylations in cancer cells: Where do they come from?" Cancer Science, vol. 96, No. 4, Apr. 2005, pp. 206-211.

Verma M: "Viral Genes and Methylation" Annals of the New York Academy of Sciences 200303 US, vol. 983, Mar. 2003, pp. 170-180.

Widschwendter et al.: "Analysis Of Aberrant DNA Methylation And Human Papillomavirus DNA In Cervicovaginal Specimens To Detect Invasive Cervical Cancer And Its Precursors" Clinical Cancer Research, The American Association For Cancer Research, US, vol. 10, No. 10, May 15, 2004, pp. 3396-3400.

Yanagi et al., "Hepatitis C Virus: An Infectious Molecular Clone of a Second Major Genotype (2A) and Lack of Viability of Intertypic 1A and 2A Chimeras," Virology 262, pp. 250-263 (1999).

Zeschnigk et al., "A novel real-time PCR assay for quantitative analysis of methylated alleles (QAMA): analysis of the retinoblastoma locus," Nucleic Acid Research 2004, vol. 32, No. 16, pp. 1-5.

* cited by examiner

METHODS FOR GENOME AMPLIFICATION

CROSS-REFERENCE TO RELATED APPLICATIONS

This application is the U.S. National Phase filing under 35 U.S.C. §371 of PCT/AU2004/000722, filed May 31, 2004, which designated the United States and was published in English, which claims priority to Australian Patent Application Nos. 2003903034 and 2003903039, both filed Jun. 17, 2003.

BACKGROUND ART

Whole Genome Amplification (WGA) of genomic DNA has been previously described. The methods have generally been based on Degenerate Oligonucleotide Primed PCR (1992 Telenius, H, et al, Genomics, 13, 718-725). Although these techniques have been shown to produce some degree of random genomic amplification, the methods have been limited in the size of the DNA fragments amplified. Using Taq polymerase (Taq) amplified representations have generally been limited to fragments varying in size from 100-2000 bp thus limiting the usefulness of these methods. By using cocktails that contain a polymerase and an additional proof reading enzyme, larger fragments up to 10 kb in size have been reported. The use of proof reading polymerase enzymes on bisulphite-treated DNA, however, generally yield no amplification due to the inherent proof reading capabilities of these polymerases which do not recognize the uracil bases in bisulphite-modified DNA (Sakaguchi, A. Y., et al Biotechniques. 1996 September; 21 (3):368-70.).

More recently, another method for WGA has been described. This method, termed Rolling Circle Amplification (RCA), is an isothermal amplification strategy employing the enzyme phi29 (2002 Dean et al, PNAS, 99(8), 5261-5266). This method does not depend on denaturation of template molecules at every cycle of the reaction unlike conventional amplification technologies. The enzyme phi29 will continually produce a DNA amplification product at 30° C. via a rolling circle method of amplification (2002 Dean et al, PNAS, 99(8), 5261-5266). In addition, using this method on normal DNA, primers as short as 6 bp have been found to be adequate for WGA. However, the phi29 enzyme has inherent exonuclease activity, thus enzyme resistant primers must be used. Using this strategy, amplified products in excess of 30 kb in size have been achieved from normal DNA (2002 Dean et al, PNAS, 99(8), 5261-5266).

The unique nature of bisulphite-modified DNA, (in which the complementary strands become different in sequence after bisulphite treatment), means that traditional methods for WGA cannot be applied. This is due to the fact that after bisulphite treatment the two DNA strands are no longer complementary. Thus to perform WGA on bisulphite-treated DNA, at least 2 primers of different sequence have to be added to an amplification reaction to target each strand of the DNA, rather than the one that would be used for amplification of normal DNA.

In addition conventional bisulphite treatment of DNA has been shown to result in the loss of up to 96% of the starting DNA (2001, Grunau C et al, Nucleic Acids Research, 1:29 (13):E65-5). The use of such DNA would not be suitable for the use in WGA methods as most of the DNA has been lost therefore any representation obtained would not be a true reflection of the original starting material.

The present inventor has now developed methods for WGA that can be used to amplify genomic DNA that has undergone bisulphite treatment.

DISCLOSURE OF INVENTION

In a first aspect, the present invention provides a method for whole genome amplification comprising:
(a) treating genomic DNA with a modifying agent which modifies cytosine bases but does not modify 5'-methylcytosine bases under conditions to form single stranded modified DNA;
(b) providing a population of random X-mers of exonuclease-resistant primers capable of binding to at least one strand of the modified DNA, wherein X is an integer 3 or greater;
(c) providing polymerase capable of amplifying double stranded DNA, together with nucleotides and optionally any suitable buffers or diluents to the modified DNA; and
(d) allowing the polymerase to amplify the modified DNA.

Preferred conditions used in step (a) do not result in substantial DNA fragmentation.

The modifying agent is preferably selected from bisulphite, acetate or citrate. More preferably, the agent is sodium bisulphite, a reagent, which in the presence of water, modifies cytosine into uracil.

Sodium bisulphite ($NaHSO_3$) reacts readily with the 5,6-double bond of cytosine to form a sulfonated cytosine reaction intermediate which is susceptible to deamination, and in the presence of water gives rise to a uracil sulfite. If necessary, the sulfite group can be removed under mild alkaline conditions, resulting in the formation of uracil. Thus, potentially all cytosines will be converted to uracils. Any methylated cytosines, however, cannot be converted by the modifying reagent due to protection by methylation.

Preferably, the exonuclease-resistant primers are oligonucleotides or oligonucleotide analogues containing at least one intercalator pseudonucleotide forming an intercalating nucleic acid (INA) as defined herein.

The oligonucleotide or oligonucleotide analogue is preferably selected from the group consisting of subunits of DNA, RNA, peptide nucleic acid (PNA), hexitol nucleic acid (HNA), MNA, altritol nucleic acid (ANA), locked nucleic acid (LNA), cyclohexanyl nucleic acid (CAN), CeNA, TNA, (2'-NH)-TNA, nucleic acid based conjugates, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0] amide-DNA, β-D-Ribopyranosyl-NA, α-L-Lyxopyranosyl-NA, 2'-R-RNA, 2'-OR-RNA, α-L-RNA, and β-D-RNA.

More preferably, the exonuclease-resistant primers are intercalating nucleic acids (INAs) formed from oligonucleotides.

Preferably, the primers contain about 3 to 40 bases. Preferably the oligonucleotide primers contain about 6 to 40 bases. It will be appreciated, however, that the primers can be any suitable length which will confer specificity to a given region of DNA.

Preferably, the random primers are formed of two population of INA primers, the first population being random X-mers containing the bases A, G and T, and the second population comprising random X-mers containing the bases A, C and T.

Preferably, the primers contain about 3 to 40 bases. More preferably, the primers contain about 6 to 20 bases. It will be appreciated, however, that the primers can be any suitable length which will confer specificity to a given region of DNA.

Preferably, one population of primers is capable of binding to one strand of DNA while the other population of primers is capable of binding to a complimentary synthesized strand of the DNA stand to which the first population of primers bind.

In one preferred embodiment, the polymerase is selected from phi29 or a modified version thereof, or a functional equivalent thereof. The polymerase is phi29 polymerase (Dean F B et al (2002), Proc, Natl. Acad. Sci, 99(8), 5261-5266). Phi29 polymerase replication of DNA does not require a periodic denaturation of the template DNA to remove the newly replicated strand. This replication step can be carried out at around 30° C. degrees for example and allowed to proceed to completion.

At present, phi29 polymerase is the first isolated polymerase which is capable of amplifying double stranded DNA in vitro without the need to denature the DNA as required for Taq polymerase for example. It will be appreciated, however, that any other polymerase with the characteristics of phi29 polymerase would also be suitable for the present invention.

In another preferred embodiment, step (c) comprises providing a polymerase cocktail comprising a mixture of at least one proof-reading DNA polymerase and at least one non proof-reading DNA polymerase, wherein the ratio of proof-reading polymerase to non proof-reading polymerase is at least about 1:2, together with nucleotides and optionally any suitable buffers or diluents to the modified DNA.

Preferably, the proof-reading DNA polymerase is selected from Pfu polymerase, Pfu polymerase turbo, Vent polymerase, Vent exo-polymerase, Pwo polymerase, 9°N$_m$ DNA polymerase, Therminator, Pfx DNA polymerase, Expand DNA polymerase, rTth DNA polymerase, DyNAzyme™ EXT Polymerase.

Preferably, the non proof-reading DNA polymerase is selected from Taq polymerase, Taq polymerase Stoffel fragment, Advantage DNA polymerase, AmpliTaq, Amplitaq Gold, Titanium Taq polymerase, KlenTaq DNA polymerase, Platinum Taq polymerase, Accuprime Taq polymerase.

Preferably, the ratio of proof-reading polymerase to non-proof-reading polymerase is at least about 1:5, more preferably about 1:10. It will be appreciated that the ratio will depend on the combination of actual polymerases used.

In a preferred embodiment, step (d) is carried out by DNA thermal cycling.

Preferred conditions for amplification include, but not limited to, DNA sample, either denatured or not, is added to an appropriate volume of sample buffer. For each reaction an appropriate volume of reaction buffer is combined with polymerase and the material mixed by vortexing. The polymerase mix is then combined with the DNA/sample buffer. The amplification reaction is then left at 30° C. for about 4-16 hours. The polymerase can be heat denatured at 65° C. for 10 minutes. The amplified DNA is then stored at −20° C. until required.

In a second aspect, the present invention provides a population of random X-mers of exonuclease-resistant primers capable of binding to at least one strand of the modified DNA in whole genome amplification, where X is an integer of 3 or greater.

Preferably, the population of primers are intercalating nucleic acids (INAs) formed from oligonucleotides. The primers are preferably formed of two populations of INA primers, the first population being random X-mers containing the bases A, G and T, and the second population comprising random X-mers containing the bases A, C and T. In a preferred embodiment, one population of primers is capable of binding to one strand of DNA while the other population of primers is capable of binding to a complimentary synthesized strand of the DNA stand to which the first population of primers bind. The population of primers preferably contain from 3 to 40 bases, more preferably about 6 to 20 bases.

In a third aspect, the present invention provides a kit containing a population of primers according to the second aspect of then present invention for use in whole genome amplification.

In a fourth aspect, the present invention provides use of a population of primers according to the second aspect of then present invention for whole genome amplication.

In a fifth aspect, the present invention provides a kit containing a population of primers according to the second aspect of then present invention, and a polymerase capable of amplifying double stranded DNA for use in whole genome amplification.

Preferably, the polymerase is polymerase is selected from phi29, or a modified version thereof, or a functional equivalent thereof capable of amplifying double stranded DNA in vitro without the need to denature the DNA; or polymerase cocktail comprising a mixture of at least one proof-reading DNA polymerase and at least one non proof-reading DNA polymerase.

An advantage of the present invention is that large amounts of genomic DNA can be amplified from small samples without significant mis-reading or loss of DNA.

A further advantage of the present invention is that there is no requirement for thermal cycling to amplify the DNA.

The present inventor has found that using exonuclease-resistant primers and polymerases such as phi29 or utilizing a unique blend of thermostable polymerases capable of amplifying bisulphite treated DNA results in the amplification of large >10 kb DNA fragments unlike conventional approaches such as Degenerate Oligonucleotide Primed-PCR.

An advantage of the present invention is that large amounts of genomic DNA can be amplified from small samples without significant mis-reading or loss of DNA.

The present invention is particularly suitable for amplification of genomic DNA from materials that may be precious or in very limited supply. Examples include, but not limited to, archival material stored on slides or in paraffin blocks, small cell numbers laser dissected samples, sampled from sources such as developing human blastocysts to be used in in vitro fertilization, circulating cancerous cells, pre-neoplastic or neoplastic cells from bone marrow, clinical samples, biopsies and small cell samples from forensic investigations.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

MODES FOR CARRYING OUT THE INVENTION

Materials and Methods

Reagents

Figure 1:
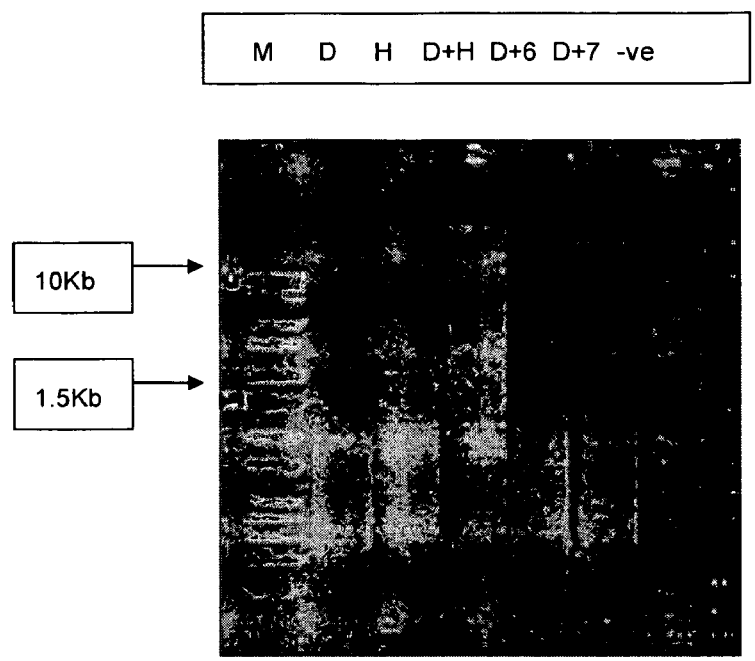
FIG. 1 shows the results of using the D and H populations of primers on bisulphite modified DNA to achieve amplification. Lane 1: WGA amplification using D population primers of length 15. Lane 2: WGA amplification using H population primers of length 15. Lane 3: WGA amplification using both D15 population primers and H15 population primers. Lane 4: WGA amplification using D+6 primer only (TTYGAGHH-HHHHMGYGA). Lane 5: WGA amplification using D+7 primer only (TTYGAGHHHHHHHAAGYGA). Lane 6: Negative control. NB. Primers D+6 and D+7 were based on the primers used by 1992 Telenius. H, et al Genomics, 13, 718-725 but modified so that N population primers were substituted with H for optimal amplification of bisulphite treated DNA

Chemicals were obtained as follows: Agarose from Bio-Rad (Hercules Calif.; certified molecular biology grade #161-3101); Acetic acid, glacial, from BDH (Kylsyth, Australia; AnalaR 100015N); ethylenediamine tetraacetic acid (EDTA) from BDH (AnalaR 10093.5V); Ethanol from Aldrich (St. Louis Mo.; 200 proof E702-3); Isopropanol from Sigma (St. Louis Mo.; 99%+ Sigma 1-9516); Mineral oil from Sigma (M-5904); Sodium acetate solution 3M from Sigma (S-7899); Sodium chloride from Sigma (ACS reagent S9888); and Sodium hydroxide from BDH (AnalaR #10252.4X).

PCR master mix from Promega (Madison Wis.; #M7505); and DNA markers from Sigma (Direct load PCR low ladder 100-1000 bp, Sigma D-3687 and 100-10 Kb, Sigma D-7058).

Solutions were as follows: (1) 10 mM Tris/0.1M EDTA, pH 7.0-12.5; (2) 3M NaOH (6 g in 50 ml water; BDH AnalaR #10252.4X); (3) 2M Metabisulphite (7.6 g in 20 ml water with 416 µl 10 N NaOH (BDH AnalaR #10356.4D); (5) 50×TAE gel electrophoresis buffer (242 g Trizma base, 57.1 ml glacial acetic acid, 37.2 g EDTA and water to 1 l); and (6) 5× Agarose gel loading buffer (1 ml 1% Bromophenol blue (Sigma B6131), 1 ml Xylene Cyanol (Sigma X-4126), 3.2 ml Glycerol (Sigma G6279), 8 µl 0.5M EDTA pH 8.0, 200 µl 50×TAE buffer and water to 10 ml).

Tissues and Cell Lines

Tissues and cell lines were obtained as follows: HeLa (cervical cancer cell line, ATCC CCL-2); LNCaP (prostate cancer cell line, ATCC #CRL-10995); HepG2 (liver cancer cell line, ATCC #HB-8065); and MCF-7 (breast cancer cell line, ATCC #HTB-22) were obtained from American Type Culture Collection.

For preparation of T-medium for growth of LNCaP Cells, reagents were obtained from Gibco/BRL or Invitrogen, except as indicated, as follows: DMEM powder 10x sachets (10×1I; #31600-034); F-12K Nutrient mixture, Kaighn's Modifn (500 ml; #21127-022); L-Glutamine, 200 mM (100 ml; #25030-081); Penicillin/Streptomycin 5000 U/ml, 5000 µg/ml (100 ml #15070-063 Thermo Trace); Foetal Bovine serum (500 ml; #15-010-0500V Sigma); Insulin (Bovine pancreas) (100 mg; #11882); Transferrin (Human) (10 mg; # T5391); d-Biotin (500 mg; #B4639); Adenine (5 g; # A3159); T3 (#T6397 or #T5516).

T-media (500 ml) was prepared as follows: DMEM stock solution was prepared by adding 3.7 g Sodium bicarbonate per liter and adjusting the pH to between 7.2-7.4. To 400 ml of DMEM stock solution, the following reagents were added: 100 ml of F-12K; 250 µl of insulin (10 mg/ml); 1.0 ml T3 (500×; Tri-iodothyronine; 6.825 ng/ml); 1.0 ml transferrin (500×; 2.5 mg/ml); 1.0 ml Biotin (500×; 0.122 mg/ml); 4.0 ml Adenine (125×; 3.125 mg/ml); 5.5 ml Penicillin/Streptomycin (100×; 5000 µg/ml); and 5.5 ml Glutamine (100×; 200 mM). After sterile filtration, 50 ml of Foetal Bovine Serum was added to give 10%.

| NAME | Cell Type | GROWING CONDITIONS |
| --- | --- | --- |
| BL13 | Bladder Cancer | RPM1 + 10% HI FCS<br>Split 1:3, 2× week |
| HeLa | Cervical Carcinoma | RPM1 + 10% HI FCS for initial rapid growth then DMEM + 10% HI FCS for slower growth.<br>Split 1:10, 2× week |
| HepG2 | Liver Carcinoma | DMEM (high glucose 4.5 g/l) + 10% HI FCS + 2 mM Glutamine.<br>Split 1:4 2× week |
| LNCAP | Prostate Cancer (Methylated) | DMEM (low glucose) + 10% HI FCS + 2 mM Glutamine + Lots of other supplements, see LNCaP growth method sheet above. |
| MCF7 | Breast Cancer | RPM1 + 10% HI FCS<br>Split 1:6, 2× week |

Purification of T-Cells and CD34+ Cells from Whole Blood

Samples were obtained from a patient undergoing leukapheresis at the Royal North Shore Hospital, Sydney. Samples were obtained with prior Ethics Committee approval. White blood cells were concentrated using Ficoll Paque plus (Amersham Biosciences #17-1440-03; Piscataway N.J.) according to the manufacturers instructions. T-cells and CD34+ cells were isolated from the white cell population using CELLection CD2 Dynabeads (Dynal #116.03; Lake Success N.Y.) and Dynal CD34 Progenitor Cell selection system (Dynal #113.01) respectively according to the manufacturers instructions.

Equipment

The following equipment was used: the PCR machine was ThermalHybaid PX2 (Sydney, Australia) the Gel Documentation System was a Kodak UVItec EDAS 290 (Rochester N.Y.), and the microfuge was an Eppendorf 5415-D (Brinkman Instruments; Westbury N.Y.).

DNA Amplification

PCR amplifications were performed in 25 µl reaction mixtures containing 2 µl of bisulphite-treated genomic DNA, using the Promega PCR master mix, 6 ng/µl of each of the primers. $1^{st}$ round PCR amplifications were carried out using the fully nested PCR primers combinations. Following $1^{st}$ round amplification 1 µl of the amplified material was transferred to $2^{nd}$ round PCR premixes containing the internal PCR primer combination and amplified in a ThermoHybaid PX2 thermal cycler under the conditions: 1 cycle of 95° C. for 4 minutes; followed by 30 cycles of 95° C. for 1 minute, 50° C. for 2 minutes and 72° C. for 2 minutes; 1 cycle of 72° C. for 10 minutes.

DNA Separation

2% agarose gels were prepared in 1% TAE containing 1 drop ethidium bromide (CLP #5450) per 50 ml of agarose. The DNA sample of interest was mixed with $\frac{1}{5}^{th}$ volume 5× agarose loading buffer and electrophoresed at 125 mA in X1 TAE using a submarine horizontal electrophoresis tank. Markers were the low 100-1000 bp type. Gels were visualised under UV irradiation using the Kodak UVIdoc EDAS 290 system.

Bisulphite Treatment of DNA

An exemplary protocol demonstrating the effectiveness of the bisulphite treatment according to the present invention is set out below. The protocol successfully resulted in retaining substantially all DNA treated. This method of the invention is also referred to herein as the Human Genetic Signatures (HGS) method. It will be appreciated that the volumes or amounts of sample or reagents can be varied.

Preferred method for bisulphite treatment can be found in U.S. application Ser. No 10/428,310 (now U.S. Pat. No. 7,288,373), which is incorporated herein by reference.

To 2 ug of DNA in a volume of 20 µl, 2.2 µl (¹⁄₁₀ volume) of 3 M NaOH (6 g in 50 ml water, freshly made). This step denatures the double stranded DNA molecules into a single stranded form, since the bisulphite reagent preferably reacts with single stranded molecules. The mixture was incubated at 37° C. for 15 minutes. Incubation at temperatures above room temperature can be used to improve the efficiency of denaturation.

After the incubation, 208 µl 2 M Sodium Metabisulphite (7.6 g in 20 ml water with 416 ml 10 N NaOH; BDH AnalaR #10356.4D; freshly made) was added in succession. The sample was overlaid with 200 µl of mineral oil. The overlaying of mineral oil prevents evaporation and oxidation of the reagents but is not essential. The sample was then incubated overnight at 55° C.

After the treatment with Sodium Metabisulphite, the oil was removed, and 1 µl tRNA (20 mg/ml) or 1 µl glycogen were added if the DNA concentration was low. These additives are optional and can be used to improve the yield of DNA obtained by co-precitpitating with the target DNA especially when the DNA is present at low concentrations.

An isopropanol cleanup treatment was performed as follows: 800 µl of water were added to the sample, mixed and then 1 ml 100% isopropanol was added. The water or buffer reduces the concentration of the bisulphite salt in the reaction vessel to a level at which the salt will not precipitate along with the target nucleic acid of interest.

The sample was mixed again and left at 4° C. for a minimum of 30 minutes. The sample was spun in a microfuge for 10-15 minutes and the pellet was washed 2× with 80% ETOH, vortexing each time. This washing treatment removed any residual salts that precipitated with the nucleic acids.

The pellet was allowed to dry and then resuspended in a suitable volume of T/E (10 mM Tris/0.1 mM EDTA) pH 7.0-12.5 such as 50 µl. Buffer at pH 10.5 has been found to be particularly effective. The sample was incubated at 37° C. to 95° C. for 1 min to 96 hr, as needed to suspend the nucleic acids. The use of the above methods does not lead to degradation of the genomic DNA during the bisulphite conversion procedure unlike conventional bisulphite methods that have been shown to result in the loss of up to 96% of the starting DNA (2001, Grunau C et al, Nucleic Acids Research, 1:29 (13):E65-5). Therefore the bisulphite treated DNA can now be used in WGA to obtain a true representation of the original starting DNA template.

Nucleic Acids

The term "nucleic acid" covers the naturally occurring nucleic acids, DNA and RNA and their methylated or unmethylated derivatives thereof. The term "nucleic acid analogues" covers derivatives of the naturally occurring nucleic acids, DNA and RNA, as well as synthetic analogues of naturally occurring nucleic acids. Synthetic analogues comprise one or more nucleotide analogues. The term nucleotide analogue includes all nucleotide analogues capable of being incorporated into a nucleic acid backbone and capable of specific base-pairing (see below), essentially like naturally occurring nucleotides.

The term "nucleic acid" also covers methylated DNA, methylated RNA, DNA containing adducts and RNA covalently bound to proteins.

Hence the terms "nucleic acid" or "nucleic acid analogues" designate any molecule which essentially consists of a plurality of nucleotides and/or nucleotide analogues and/or intercalator pseudonucleotides. Nucleic acids or nucleic acid analogues useful for the present invention may comprise a number of different nucleotides with different backbone monomer units.

Preferably, single strands of nucleic acids or nucleic acid analogues are capable of hybridising with a substantially complementary single stranded nucleic acid and/or nucleic acid analogue to form a double stranded nucleic acid or nucleic acid analogue. More preferably such a double stranded analogue is capable of forming a double helix. Preferably, the double helix is formed due to hydrogen bonding, more preferably, the double helix is a double helix selected from the group consisting of double helices of A form, B form, Z form and intermediates thereof.

Hence, nucleic acids and nucleic acid analogues useful for the present invention include, but is not limited to DNA, RNA, LNA, PNA, MNA, ANA, HNA, INA and mixtures thereof and hybrids thereof, as well as phosphorous atom modifications thereof, such as but not limited to phosphorothioates, methyl phospholates, phosphoramidites, phosphorodithiates, phosphoroselenoates, phosphotriesters and phosphoboranoates. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more intercalator pseudonucleotides to form an INA.

Within this context "mixture" is meant to cover a nucleic acid or nucleic acid analogue strand comprising different kinds of nucleotides or nucleotide analogues. Furthermore, within this context, "hybrid" is meant to cover nucleic acids or nucleic acid analogues comprising one strand which comprises nucleotide or nucleotide analogue with one or more kinds of backbone and another strands which comprises nucleotide or nucleotide analogue with different kinds of backbone.

By INA is meant an intercalating nucleic acid in accordance with the teaching of WO 03/051901, WO 03/052132, WO 03/052133 and WO 03/052134 (Unest A/S) incorporated herein by reference. An INA is an oligonucleotide or oligonucleotide analogue comprising one or more intercalator pseudonucleotide (IPN) molecules.

By HNA is meant nucleic acids as for example described by Van Aetschot et al., 1995. By MNA is meant nucleic acids as described by Hossain et al, 1998. ANA refers to nucleic acids described by Allert et al, 1999. LNA may be any LNA molecule as described in WO 99/14226 (Exiqon), preferably, LNA is selected from the molecules depicted in the abstract of WO 99/14226. More preferably, LNA is a nucleic acid as described in Singh et al, 1998, Koshkin et al, 1998 or Obika et al., 1997. PNA refers to peptide nucleic acids as for example described by Nielsen et al, 1991.

The term nucleotide designates the building blocks of nucleic acids or nucleic acid analogues and the term nucleotide covers naturally occurring nucleotides and derivatives thereof as well as nucleotides capable of performing essentially the same functions as naturally occurring nucleotides and derivatives thereof. Naturally occurring nucleotides comprise deoxyribonucleotides comprising one of the four main nucleobases adenine (A), thymine (T), guanine (G) or cytosine (C), and ribonucleotides comprising on of the four nucleobases adenine (A), uracil (U), guanine (G) or cytosine (C). In addition to the main or common bases above, other less common naturally occurring bases which can exist in some nucleic acid molecules include 5-methyl cytosine (met-C) and 6-methyl adenine (met-A).

Nucleotide analogues may be any nucleotide like molecule that is capable of being incorporated into a nucleic acid backbone and capable of specific base-pairing. Non-naturally occurring nucleotides includes, but is not limited to the nucleotides comprised within DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA.

The function of nucleotides and nucleotide analogues is to be able to interact specifically with complementary nucleotides via hydrogen bonding of the nucleobases of the complementary nucleotides as well as to be able to be incorporated into a nucleic acid or nucleic acid analogue. Naturally occurring nucleotide, as well as some nucleotide analogues are capable of being enzymatically incorporated into a nucleic acid or nucleic acid analogue, for example by RNA or DNA polymerases. However, nucleotides or nucleotide analogues may also be chemically incorporated into a nucleic acid or nucleic acid analogue.

Furthermore nucleic acids or nucleic acid analogues may be prepared by coupling two smaller nucleic acids or nucleic acid analogues to another, for example this may be done enzymatically by ligases or it may be done chemically.

Nucleotides or nucleotide analogues comprise a backbone monomer unit and a nucleobase. The nucleobase may be a naturally occurring nucleobase or a derivative thereof or an analogue thereof capable of performing essentially the same function. The function of a nucleobase is to be capable of associating specifically with one or more other nucleobases via hydrogen bonds. Thus it is an important feature of a nucleobase that it can only form stable hydrogen bonds with one or a few other nucleobases, but that it can not form stable hydrogen bonds with most other nucleobases usually including itself. The specific interaction of one nucleobase with another nucleobase is generally termed "base-pairing".

The base pairing results in a specific hybridisation between predetermined and complementary nucleotides. Complementary nucleotides are nucleotides that comprise nucleobases that are capable of base-pairing.

Of the common naturally occurring nucleobases, adenine (A) pairs with thymine (T) or uracil (U); and guanine (G) pairs with cytosine (C). Accordingly, a nucleotide comprising A is complementary to a nucleotide comprising either T or U, and a nucleotide comprising G is complementary to a nucleotide comprising C.

Nucleotides may further be derivatized to comprise an appended molecular entity. The nucleotides can be derivatized on the nucleobases or on the backbone monomer unit. Preferred sites of derivatization on the bases include the 8-position of adenine, the 5-position of uracil, the 5- or 6-position of cytosine, and the 7-position of guanine. The heterocyclic modifications can be grouped into three structural classes: Enhanced base stacking, additional hydrogen bonding, and the combination of these classes. Modifications that enhance base stacking by expanding the π-electron cloud of the planar systems are represented by conjugated, lipophilic modifications in the 5-position of pyrimidines and the 7-position of 7-deaza-purines. Substitutions in the 5-position of pyrimidines modifications include propynes, hexynes, thiazoles and simply a methyl group; and substituents in the 7-position of 7-deaza purines include iodo, propynyl, and cyano groups. It is also possible to modify the 5-position of cytosine from propynes to five-membered heterocycles and to tricyclic fused systems, which emanate from the 4- and 5-position (cytosine clamps). A second type of heterocycle modification is represented by the 2-amino-adenine where the additional amino group provides another hydrogen bond in the A-T base pair, analogous to the three hydrogen bonds in a G-C base pair. Heterocycle modifications providing a combination of effects are represented by 2-amino-7-deaza-7-modified adenine and the tricyclic cytosine analog having an ethoxyamino functional group of heteroduplexes. Furthermore, N2-modified 2-amino adenine modified oligonucleotides are among commonly modifications. Preferred sites of derivatisation on ribose or deoxyribose moieties are modifications of non-connecting carbon positions C-2' and C-4', modifications of connecting carbons C-1', C-3' and C-5', replacement of sugar oxygen, O-4', anhydro sugar modifications (conformational restricted), cyclosugar modifications (conformational restricted), ribofuranosyl ring size change, connection sites—sugar to sugar, (C-3' to C-5'/C-2' to C-5'), hetero-atom ring—modified sugars and combinations of above modifications. However, other sites may be derivatised, as long as the overall base pairing specificity of a nucleic acid or nucleic acid analogue is not disrupted. Finally, when the backbone monomer unit comprises a phosphate group, the phosphates of some backbone monomer units may be derivatised.

Oligonucleotide or oligonucleotide analogue as used herein are molecules essentially consisting of a sequence of nucleotides and/or nucleotide analogues and/or intercalator pseudonucleotides. Preferably oligonucleotide or oligonucleotide analogue comprises 5 to 100 individual nucleotides. Oligonucleotide or oligonucleotide analogues may comprise DNA, RNA, LNA, 2'-O-methyl RNA, PNA, ANA, HNA and mixtures thereof, as well as any other nucleotide and/or nucleotide analogue and/or intercalator pseudonucleotide.

Corresponding Nucleic Acids

Nucleic acids, nucleic acid analogues, oligonucleotides or oligonucleotide analogues are considered to be corresponding when they are capable of hybridising. Preferably corresponding nucleic acids, nucleic acid analogues, oligonucleotides or oligonucleotide analogues are capable of hybridising under low stringency conditions, more preferably corresponding nucleic acids, nucleic acid analogues, oligonucleotides or oligonucleotide analogues are capable of hybridising under medium stringency conditions, more preferably corresponding nucleic acids, nucleic acid analogues, oligonucleotides or oligonucleotide analogues are capable of hybridising under high stringency conditions.

High stringency conditions as used herein shall denote stringency as normally applied in connection with Southern blotting and hybridisation as described e.g. by Southern E. M., 1975, J. Mol. Biol. 98:503-517. For such purposes it is routine practise to include steps of prehybridization and hybridization. Such steps are normally performed using solutions containing 6×SSPE, 5% Denhardt's, 0.5% SDS, 50% formamide, 100 µg/ml denatured salmon testis DNA (incubation for 18 hrs at 42° C.), followed by washing with 2×SSC and 0.5% SDS (at room temperature and at 37° C.), and washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

Medium stringency conditions as used herein shall denote hybridisation in a buffer containing 1 mM EDTA, 10 mM $Na_2HPO_4.H_2O$, 140 mM NaCl, at pH 7.0. Preferably, around 1.5 µM of each nucleic acid or nucleic acid analogue strand is provided. Alternatively medium stringency may denote hybridisation in a buffer containing 50 mM KCl, 10 mM TRIS-HCl (pH 9,0), 0.1% Triton X-100, 2 mM MgCl2.

Low stringency conditions denote hybridisation in a buffer constituting 1 M NaCl, 10 mM $Na_3PO_4$ at pH 7,0.

Alternatively, corresponding nucleic acids, nucleic acid analogues, oligonucleotides or oligonucleotides, nucleic acid analogues, oligonucleotides or oligonucleotides substantially complementary to each other over a given sequence, such as more than 70% complementary, for example more than 75% complementary, such as more than 80% complementary, for example more than 85% complementary, such as more than 90% complementary, for example more than 92% complementary, such as more than 94% complementary, for example more than 95% complementary, such as more than 96% complementary, for example more than 97% complementary.

Preferably the given sequence is at least 10 nucleotides long, such as at least 15 nucleotides, for example at least 20 nucleotides, such as at least 25 nucleotides, for example at least 30 nucleotides, such as between 10 and 500 nucleotides, for example between 10 and 100 nucleotides long, such as between 10 and 50 nucleotides long. More preferably corresponding oligonucleotides or oligonucleotide analogues are substantially complementary over their entire length.

Cross-Hybridisation

The term cross-hybridisation covers unintended hybridisation between at least two nucleic acids or nucleic acid analogues. Hence the term cross-hybridization may be used to describe the hybridisation of for example a nucleic acid probe or nucleic acid analogue probe sequence to other nucleic acid sequences or nucleic acid analogue sequences than its intended target sequence.

Often cross-hybridization occurs between a probe and one or more corresponding non-target sequences, even though these have a lower degree of complementarity than the probe and its corresponding target sequence. This unwanted effect could be due to a large excess of probe over target and/or fast annealing kinetics. Cross-hybridization also occurs by hydrogen bonding between few nucleobase pairs, e.g. between primers in a PCR reaction, resulting in primer dimer formation and/or formation of unspecific PCR products.

Nucleic acids comprising one or more nucleotide analogues with high affinity for nucleotide analogues of the same type tend to form dimer or higher order complexes based on base pairing. Probes comprising nucleotide analogues such as, but not limited to, LNA, 2'-O-methyl RNA and PNA generally have a high affinity for hybridising to other oligonucleotide analogues comprising backbone monomer units of the same type. Hence even though individual probe molecules only have a low degree of complementarity they tend to hybridize.

Self-Hybridisation

The term self-hybridisation covers the process wherein a nucleic acid or nucleic acid analogue molecule anneals to itself by folding back on itself, generating a secondary structure like for example a hairpin structure, or one molecule binding to another identical molecule leading to aggregation of the molecules. In most applications it is of importance to avoid self-hybridization. Furthermore, self hybridization can also increase background signal and importantly decrease the sensitivity of molecular biological methods or assays. The generation of secondary structures may inhibit hybridisation with desired nucleic acid target sequences. This is undesired in most assays for example when the nucleic acid or nucleic acid analogue is used as primer in PCR reactions or as fluorophore/quencher labelled probe for exonuclease assays. In both assays, self-hybridisation will inhibit hybridization to the target nucleic acid and additionally the degree of fluorophore quenching in the exonuclease assay is lowered.

Nucleic acids comprising one or more nucleotide analogues with high affinity for nucleotide analogues of the same type tend to self-hybridize. Probes comprising nucleotide analogues such as, but not limited to, LNA, 2'-O-methyl RNA and PNA generally have a high affinity for self-hybridising. Hence even though individual probe molecules only have a low degree of self-complementary they tend to self-hybridize.

Melting Temperature

Melting of nucleic acids refer to the separation of the two strands of a double-stranded nucleic acid molecule. The melting temperature ($T_m$) denotes the temperature in degrees celcius at which 50% helical (hybridized) versus coil (unhybridized) forms are present.

A high melting temperature is indicative of a stable complex and accordingly of a high affinity between the individual strands. Similarly, a low melting temperature is indicative of a relatively low affinity between the individual strands. Accordingly, usually strong hydrogen bonding between the two strands results in a high melting temperature.

Furthermore, intercalation of an intercalator between nucleobases of a double stranded nucleic acid may also stabilise double stranded nucleic acids and accordingly result in a higher melting temperature.

In addition, the melting temperature is dependent on the physical/chemical state of the surroundings. For example the melting temperature is dependent on salt concentration and pH.

The melting temperature may be determined by a number of assays, for example it may be determined by using the UV spectrum to determine the formation and breakdown (melting) of hybridisation.

Intercalator Pseudonucleotide (IPN)

Pseudonucleotides or polynucleotide analogues comprising intercalators and having one or more of the following desirable characteristics:

Intercalate into the double helix at a predetermined position;
Substantially increase the affinity for DNA;
Inhibit or decrease self and cross hybridisation;
Discriminate between different nucleic acids, such as RNA and DNA;
Substantially increase the specificity of hybridisation;
Increase nuclease stability;
Enhance strand invasion significantly;
Show a change in fluorescence intensity upon hybridisation.

An intercalator pseudonucleotide (IPN) has the general structure:

X—Y-Q wherein

X is a backbone monomer unit capable of being incorporated into the backbone of a nucleic acid or nucleic acid analogue, Q is an intercalator comprising at least one essentially flat conjugated system, which is capable of co-stacking with nucleobases of DNA; and Y is a linker moiety linking the backbone monomer unit and the intercalator. More preferably an intercalator pseudonucleotide has the general structure:

X—Y-Q wherein

X is a backbone monomer unit capable of being incorporated into the backbone of a nucleic acid or nucleic acid analogue of the general formula,

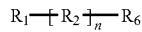

wherein n=1 to 6

$R_1$ is a trivalent or pentavalent substituted phosphor atom,
$R_2$ is individually selected from an atom capable of forming at least two bonds, $R_2$ optionally being individually substituted, and
$R_6$ is a protecting group;

Q is an intercalator comprising at least one essentially flat conjugated system, which is capable of co-stacking with nucleobases of DNA; and Y is a linker moiety linking any of $R_2$ of the backbone monomer unit and the intercalator; and wherein the total length of Q and Y is in the range from about 7 å to 20 å.

When the intercalator is pyrene, for example, the total length of Q and Y is in the range from about 9 Å to 13 Å, preferably from about 9 Å to 11 Å.

By the term "incorporated into the backbone of a nucleic acid or nucleic acid analogue" is meant that the intercalator pseudonucleotide may be inserted into a sequence of nucleic acids and/or nucleic acid analogues.

By the term "flat conjugated system" is meant that substantially all atoms included in the conjugated system are located in one plane.

By the term "essentially flat conjugated system" is meant that at most 20% of all atoms included in the conjugated system are not located in the one plane at any time.

By the term "conjugated system" is meant a structural unit containing chemical bonds with overlap of atomic p orbitals of three or more adjacent atoms (Gold et al., 1987. Compendium of Chemical Terminology, Blackwell Scientific Publications, Oxford, UK).

Co-stacking is used in short for coaxial stacking. Coaxial stacking is an energetically favorable structure where flat molecules align on top of each other (flat side against flat side) along a common axis in a stack-like structure. Co-stacking requires interaction between two pi-electron clouds of individual molecules. In the case of intercalator pseudonucleotides, co-stacking with nucleobases in a duplex, preferably there is an interaction with a pi electron system on an opposite strand, more preferably there is interaction with pi electron systems on both strands. Co-stacking interactions are found both inter- and intra-molecularly. For example nucleic acids adopt a duplex structure to allow nucleobase co-stacking.

Furthermore, the intercalator pseudonucleotide comprises a backbone monomer unit, wherein the backbone monomer unit is capable of being incorporated into the phosphate backbone of a nucleic acid or nucleic acid analogue in a manner so that at the most 4 atoms are separating the two phosphor atoms of the backbone that are closest to the intercalator.

The intercalator pseudonucleotides preferably do not comprise a nucleobase capable of forming Watson-Crick hydrogen bonding. Hence intercalator pseudonucleotides are preferably not capable of Watson-Crick base pairing.

Preferably, the total length of Q and Y is in the range from about 7 Å to 20 Å, more preferably, from about 8 Å to 15 Å, even more preferably from about 8 Å to 13 Å, even more preferably from about 8.4 Å to 12 Å, most preferably from about 8.59 Å to 10 Å or from about 8.4 Å to 10.5 Å.

When the intercalator is pyrene for example, the total length of Q and Y is preferably in the range of about 8 Å to 13 Å, such as from about 9 Å to 13 Å, more preferably from about 9.05 Å to 11 Å, such as from about 9.0 Å to 11 Å, even more preferably from about 9.05 to 10 Å, such as from about 9.0 to 10 Å, most preferably about 9.8 Å.

The total length of the linker (Y) and the intercalator (Q) should be determined by determining the distance from the center of the non-hydrogen atom of the linker which is furthest away from the intercalator to the center of the non-hydrogen atom of the essentially flat, conjugated system of the intercalator that is furthest away from the backbone monomer unit. Preferably, the distance should be the maximal distance in which bonding angles and normal chemical laws are not broken or distorted in any way.

The distance should preferably be determined by calculating the structure of the free intercalator pseudonucleotide with the lowest conformational energy level, and then determining the maximum distance that is possible from the center of the non-hydrogen atom of the linker which is furthest away from the intercalator to the center of the non-hydrogen atom of the essentially flat, conjugated system of the intercalator that is furthest away from the backbone monomer unit without bending, stretching or otherwise distorting the structure more than simple rotation of bonds that are free to rotate (e.g. not double bonds or bonds participating in a ring structure). Preferably the energetically favorable structure is found by ab initio or force fields calculations.

The distance can be determined by a method consisting of the following steps:

the structure of the intercalator pseudonucleotide of interest is drawn by computer using the programme ChemWindow® 6.0 (BioRad);

the structure is transferred to the computer programme SymApps™ (BioRad);

the 3-dimensional structure comprising calculated lengths of bonds and bonding angles of the intercalator pseudonucleotide is calculated using the computer programme SymApps™ (BioRad);

the 3 dimensional structure is transferred to the computer programme RasWin Molecular Graphics Ver. 2.6-ucb;

the bonds are rotated using RasWin Molecular Graphics Ver. 2.6-ucb to obtain the maximal distance (the distance as defined herein above); and the distance is determined.

Intercalator pseudonucleotides may be any combination of the above mentioned backbone monomer units, linkers and intercalators.

In another preferred form, the intercalator pseudonucleotide is selected from the group consisting of phosphoramidites of 1-(4,4'-dimethoxytriphenylmethyloxy)-3-pyrenemethyloxy-2-propanol. Even more preferably, the intercalator pseudonucleotide is selected from the group consisting of the phosphoramidite of (S)-1-(4,4'-dimethoxytriphenylmethyloxy)-3-pyrenemethyloxy-2-propanol and the phosphoramidite of (R)-1-(4,4'-dimethoxytriphenylmethyloxy)-3-pyrenemethyloxy-2-propanol.

Backbone Monomer Unit

Any suitable backbone monomer unit may be employed. The backbone monomer unit comprises the part of an intercalator pseudonucleotide that may be incorporated into the backbone of an oligonucleotide or an oligonucleotide analogue. In addition, the backbone monomer unit may comprise one or more leaving groups, protecting groups and/or reactive groups, which may be removed or changed in any way during synthesis or subsequent to synthesis of an oligonucleotide or oligonucleotide analogue comprising the backbone monomer unit.

The term 'backbone monomer unit' only includes the backbone monomer unit per se and it does not include, for example, a linker connecting a backbone monomer unit to an intercalator. Hence, the intercalator as well as the linker is not part of the backbone monomer unit.

Accordingly, backbone monomer units only include atoms, wherein the monomer is incorporated into a sequence, are selected from the group consisting of atoms which are capable of forming a linkage to the backbone monomer unit of a neighboring nucleotide; or atoms which at least at two sites are connected to other atoms of the backbone monomer unit; or atoms which at one site is connected to the backbone monomer unit and otherwise is not connected with other atoms.

Backbone monomer unit atoms are thus defined as the atoms involved in the direct linkage (shortest path) between the backbone Phosphor-atoms of neighbouring nucleotides, when the monomer is incorporated into a sequence, wherein the neighbouring nucleotides are naturally occurring nucleotides.

The backbone monomer unit may be any suitable backbone monomer unit. The backbone monomer unit may for example be selected from the group consisting of the backbone monomer units of DNA, RNA, PNA, INA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA.

The backbone monomer unit of LNA (locked nucleic acid) is a sterically restricted DNA backbone monomer unit, which comprises an intramolecular bridge that restricts the usual conformational freedom of a DNA backbone monomer unit. LNA may be any LNA molecule as described in WO 99/14226 (Exiqon). Preferred LNA comprises a methyl linker connecting the 2'-O position to the 4'-C position, however other LNA's such as LNA's wherein the 2' oxy atom is replaced by either nitrogen or sulphur are also comprised within the present invention.

The backbone monomer unit of intercalator pseudonucleotides preferably have the general structure before being incorporated into an oligonucleotide and/or nucleotide analogue:

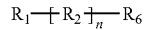

wherein n=1 to 6, preferably n=2 to 6, more preferably n=3 to 6, more preferably n=2 to 5, more preferably n=3 to 5, more preferably n=3 to 4;

$R_1$ is a trivalent or pentavalent substituted phosphor atom, preferably $R_1$ is

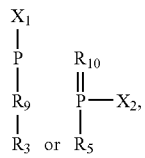

wherein $R_2$ may individually be selected from an atom capable of forming at least two bonds, the atom optionally being individually substituted, preferably $R_2$ is individually selected from O, S, N, C, P, optionally individually substituted. By the term "individually" is meant that $R_2$ can represent one, two or more different groups in the same molecule. The bonds between two $R_2$ may be saturated or unsaturated or a part of a ring system or a combination thereof. Each $R_2$ may individually be substituted with any suitable substituent, such as a substituent selected from H, lower alkyl, C2-C6 alkenyl, C6-C10 aryl, C7-C11 arylmethyl, C2-C7 acyloxymethyl, C3-C8 alkoxycarbonyloxymethyl, C7-C11 aryloyloxymethyl, C3-C8 S-acyl-2-thioethyl.

An "alkyl" group refers to an optionally substituted saturated aliphatic hydrocarbon, including straight-chain, branched-chain, and cyclic alkyl groups. Preferably, the alkyl group has 1 to 25 carbons and contains no more than 20 heteroatoms. More preferably, it is a lower alkyl of from 1 to 12 carbons, more preferably 1 to 6 carbons, more preferably 1 to 4 carbons. Heteroatoms are preferably selected from the group consisting of nitrogen, sulfur, phosphorus, and oxygen.

An "alkenyl" group refers to an optionally substituted hydrocarbon containing at least one double bond, including straight-chain, branched-chain, and cyclic alkenyl groups, all of which may be optionally substituted. Preferably, the alkenyl group has 2 to 25 carbons and contains no more than 20 heteroatoms. More preferably, it is a lower alkenyl of from 2 to 12 carbons, more preferably 2 to 4 carbons. Heteroatoms are preferably selected from the group consisting of nitrogen, sulfur, phosphorus, and oxygen.

An "alkynyl" group refers to an optionally substituted unsaturated hydrocarbon containing at least one triple bond, including straight-chain, branched-chain, and cyclic alkynyl groups, all of which may be optionally substituted. Preferably, the alkynyl group has 2 to 25 carbons and contains no more than 20 heteroatoms. More preferably, it is a lower alkynyl of from 2 to 12 carbons, more preferably 2 to 4 carbons. Heteroatoms are preferably selected from the group consisting of nitrogen, sulfur, phosphorus, and oxygen.

An "aryl" refers to an optionally substituted aromatic group having at least one ring with a conjugated pi electron system and includes carbocyclic aryl, heterocyclic aryl, bi-aryl, and tri-aryl groups. Examples of aryl substitution substituents include alkyl, alkenyl, alkynyl, aryl, amino, substituted amino, carboxy, hydroxy, alkoxy, nitro, sulfonyl, halogen, thiol and aryloxy.

A "carbocyclic aryl" refers to an aryl where all the atoms on the aromatic ring are carbon atoms. The carbon atoms are optionally substituted as described above for an aryl. Preferably, the carbocyclic aryl is an optionally substituted phenyl.

A "heterocyclic aryl" refers to an aryl having 1 to 3 heteroatoms as ring atoms in the aromatic ring and the remainder of the ring atoms are carbon atoms. Suitable heteroatoms include oxygen, sulfur, and nitrogen. Examples of heterocyclic aryls include furanyl, thienyl, pyridyl, pyrrolyl, N-lower alkyl pyrrolo, pyrimidyl, pyrazinyl, and imidazolyl. The heterocyclic aryl is optionally substituted as described above for an aryl.

The substituents on two or more $R_2$ may alternatively join to form a ring system, such as any of the ring systems as defined above. Preferably $R_2$ is substituted with an atom or a group selected from H, methyl, $R_4$, hydroxyl, halogen, and amino, more preferably $R_2$ is substituted with an atom or a group selected from H, methyl, $R_4$. More preferably $R_2$ is individually selected from O, S, NH, N(Me), N($R_4$), C($R_4$)$_2$, CH($R_4$) or CH$_2$, wherein $R_4$ is as defined below.

$R_3$ is methyl, beta-cyanoethyl, p-nitrophenetyl, o-chlorophenyl, or p-chlorophenyl.

$R_4$ is lower alkyl, preferably lower alkyl such as methyl, ethyl, or isopropyl, or heterocyclic, such as morpholino, pyrrolidino, or 2,2,6,6-tetramethylpyrrolidino, wherein lower alkyl is defined as $C_1$-$C_6$, such as $C_1$-$C_4$.

$R_5$ is alkyl, alkoxy, aryl or H, with the proviso that $R_5$ is H when $X_2$=O$^-$, preferably $R_5$ is selected from lower alkyl, lower alkoxy, aryloxy. In a preferred embodiment aryloxy is selected from phenyl, naphtyl or pyridine.

$R_6$ is a protecting group, selected from any suitable protecting groups. Preferably $R_6$ is selected from the group consisting of trityl, monomethoxytrityl, 2-chlorotrityl, 1,1,1,2-tetrachloro-2,2-bis(p-methoxyphenyl)-ethan (DATE), 9-phenylxanthine-9-yl(pixyl) and 9-(p-methoxyphenyl) xanthine-9-yl (MOX) or other protecting groups mentioned in "Current Protocols In Nucleic Acid Chemistry" volume 1, Beaucage et al. Wiley. More preferably, the protecting group may be selected from the group consisting of monomethoxytrityl and dimethoxytrityl. Most preferably, the protecting group may be 4,4'-dimethoxytrityl (DMT).

$R_9$ is selected from O, S, N optionally substituted, preferably $R_9$ is selected from O, S, NH, N(Me).

$R_{10}$ is selected from O, S, N, C, optionally substituted.

$X_1$ is selected from Cl, Br, I, or N($R_4$)$_2$ $X_2$ is selected from Cl, Br, I, N($R_4$)$_2$, or O$^-$ As described above with respect to the substituents the backbone monomer unit can be acyclic or part of a ring system.

Preferably, the backbone monomer unit of an intercalator pseudonucleotide is selected from the group consisting of acyclic backbone monomer units. Acyclic is meant to cover any backbone monomer unit, which does not comprise a ring structure, for example the backbone monomer unit preferably does not comprise a ribose or a deoxyribose group.

In particular, it is preferred that the backbone monomer unit of an intercalator pseudonucleotide is an acyclic backbone monomer unit, which is capable of stabilising a bulge insertion (defined below).

The backbone monomer unit of an intercalator pseudonucleotide may be selected from the group consisting of backbone monomer units comprising at least one chemical group selected from trivalent and pentavalent phosphorous atom such as a pentavalent phosphorous atom. More preferably, the phosphate atom of the backbone monomer unit of an intercalator pseudonucleotide may be selected from the group consisting of backbone monomer units comprising at least one chemical group selected from the group consisting of, phosphoester, phosphodiester, phosphoramidate and phosphoramidite groups.

Preferred backbone monomer units comprising at least one chemical group selected from the group consisting of phosphate, phosphoester, phosphodiester, phosphoramidate and phosphoramidite groups are backbone monomer units, wherein the distance from at least one phosphor atom to at least one phosphor atom of a neighbouring nucleotide, not including the phosphor atoms, is at the most 6 atoms long, for example 2, such as 3, for example 4, such as 5, for example 6 atoms long, when the backbone monomer unit is incorporated into a nucleic acid backbone.

Preferably, the backbone monomer unit is capable of being incorporated into a phosphate backbone of a nucleic acid or nucleic acid analogue in a manner so that at the most 5 atoms (more preferably at most 4) are separating the phosphor atom of the intercalator pseudonucleotide backbone monomer unit and the nearest neighbouring phosphor atom, more preferably 5 atoms are separating the phosphor atom of the intercalator pseudonucleotide backbone monomer unit and the nearest neighbouring phosphor atom, in both cases not including the phosphor atoms themselves.

In a particularly preferred form, the intercalator pseudonucleotide comprises a backbone monomer unit that comprises a phosphoramidite and more preferably the backbone monomer unit comprises a trivalent phosphoramidite. Suitable trivalent phosphoramidites are trivalent phosphoramidites that may be incorporated into the backbone of a nucleic acid and/or a nucleic acid analogue. Usually, the amidit group may not be incorporated into the backbone of a nucleic acid, but rather the amidit group or part of the amidit group may serve as a leaving group and/or protecting group. However, it is preferred that the backbone monomer unit comprises a phosphoramidite group because such a group may facilitate the incorporation of the backbone monomer unit into a nucleic acid backbone.

The backbone monomer unit of an intercalator pseudonucleotide which is inserted into an oligonucleotide or oligonucleotide analogue, may comprise a phosphodiester bond. Additionally, the backbone monomer unit of an intercalator pseudonucleotide may comprise a pentavalent phosphoramidate. Preferably, the backbone monomer unit of an intercalator pseudonucleotide is an acyclic backbone monomer unit that may comprise a pentavalent phosphoramidate.

Leaving Group

The backbone monomer unit may comprise one or more leaving groups. Leaving groups are chemical groups, which are part of the backbone monomer unit when the intercalator pseudonucleotide or the nucleotide is a monomer, but which are no longer present in the molecule once the intercalator pseudonucleotide or the nucleotide has been incorporated into an oligonucleotide or oligonucleotide analogue.

The nature of a leaving group depends of the backbone monomer unit. For example, when the backbone monomer unit is a phosphor amidit, the leaving group may, for example be an diisopropylamine group. In general, when the backbone monomer unit is a phosphor amidit, a leaving group is attached to the phosphor atom for example in the form of diisopropylamine and the leaving group is removed upon coupling of the phosphor atom to a nucleophilic group, whereas the rest of the phosphate group or part of the rest, may become part of the nucleic acid or nucleic acid analogue backbone.

Reactive Group

The backbone monomer units may furthermore comprise a reactive group which is capable of performing a chemical reaction with another nucleotide or oligonucleotide or nucleic acid or nucleic acid analogue to form a nucleic acid or nucleic acid analogue, which is one nucleotide longer than before the reaction. Accordingly, when nucleotides are in their free form, i.e. not incorporated into a nucleic acid, they may comprise a reactive group capable of reacting with another nucleotide or a nucleic acid or nucleic acid analogue.

The reactive group may be protected by a protecting group. Prior to the chemical reaction, the protection group may be removed. The protection group will thus not be a part of the newly formed nucleic acid or nucleic acid analogue. Examples of reactive groups are nucleophiles such as the 5'-hydroxy group of DNA or RNA backbone monomer units.

Protecting Group

The backbone monomer unit may also comprise a protecting group which can be removed during synthesis. Removal of the protecting group allows for a chemical reaction between the intercalator pseudonucleotide and a nucleotide or nucleotide analogue or another intercalator pseudonucleotide.

In particular, a nucleotide monomer or nucleotide analogue monomer or intercalator pseudonucleotide monomer may comprise a protecting group, which is no longer present in the molecule once the nucleotide or nucleotide analogue or intercalator pseudonucleotide has been incorporated into a nucleic acid or nucleic acid analogue. Furthermore, backbone monomer units may comprise protecting groups which may be present in the oligonucleotide or oligonucleotide analogue subsequent to incorporation of the nucleotide or nucleotide analogue or intercalator pseudonucleotide, but which may no longer be present after introduction of an additional nucleotide or nucleotide analogue to the oligonucleotide or oligonucleotide analogue or which may be removed after the synthesis of the entire oligonucleotide or oligonucleotide analogue.

The protecting group may be removed by a number of suitable techniques known to the person skilled in the art. Preferably, the protecting group may be removed by a treatment selected from the group consisting of acid treatment, thiophenol treatment and alkali treatment.

Preferred protecting groups, which may be used to protect the 5' end or the 5' end analogue of a backbone monomer unit may be selected from the group consisting of trityl, monomethoxytrityl, 2-chlorotrityl, 1,1,1,2-tetrachloro-2,2-bis(p-methoxyphenyl)-ethan (DATE), 9-phenylxanthine-9-yl(pixyl) and 9-(p-methoxyphenyl)xanthine-9-yl (MOX) or other protecting groups mentioned in "Current Protocols In Nucleic Acid Chemistry" volume 1, Beaucage et al. Wiley. More preferably the protecting group may be selected from the group consisting of monomethoxytrityl and dimethoxytrityl. Most preferably, the protecting group may be 4,4'-dimethoxytrityl(DMT). 4,4'-dimethoxytrityl(DMT) groups may be removed by acid treatment, for example by brief incubation (30 to 60 seconds sufficient) in 3% trichloroacetic acid or in 3% dichloroacetic acid in $CH_2Cl_2$.

Preferred protecting groups which may protect a phosphate or phosphoramidite group of a backbone monomer unit may for example be selected from the group consisting of methyl and 2-cyanoethyl. Methyl protecting groups may for example be removed by treatment with thiophenol or disodium 2-carbamoyl 2-cyanoethylene-1,1-dithiolate. 2-cyanoethyl-groups may be removed by alkali treatment, for example treatment with concentrated aqueous ammonia, a 1:1 mixture of aqueous methylamine and concentrated aqueous ammonia or with ammonia gas.

Intercalator

The term intercalator covers any molecular moiety comprising at least one essentially flat conjugated system, which is capable of co-stacking with nucleobases of a nucleic acid. Preferably an intercalator consists of at least one essentially flat conjugated system which is capable of co-stacking with nucleobases of a nucleic acid or nucleic acid analogue.

Preferably, the intercalator comprises a chemical group selected from the group consisting of polyaromates and heteropolyaromates an even more preferably the intercalator essentially consists of a polyaromate or a heteropolyaromate. Most preferably, the intercalator is selected from the group consisting of polyaromates and heteropolyaromates.

Polyaromates or heteropolyaromates may consist of any suitable number of rings, such as 1, for example 2, such as 3, for example 4, such as 5, for example 6, such as 7, for example 8, such as more than 8. Furthermore polyaromates or heteropolyaromates may be substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and amido.

In one preferred form, the intercalator may be selected from the group consisting of polyaromates and heteropolyaromates that are capable of fluorescing.

In another more preferred form, the intercalator may be selected from the group consisting of polyaromates and heteropolyaromates that are capable of forming excimers, exciplexes, fluorescence resonance energy transfer (FRET) or charged transfer complexes.

Accordingly, the intercalator may preferably be selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins, psoralens and any of the aforementioned intercalators substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and/or amido.

Preferably, the intercalator is selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins and psoralens.

The examples of intercalators are not to be understood as limiting in any way, but only as to provide examples of possible structures for use as intercalators. In addition, the substitution of one or more chemical groups on each intercalator to obtain modified structures is also included.

The intercalator moiety of the intercalator pseudonucleotide is linked to the backbone unit by the linker. When going from the backbone along the linker to the intercalator moiety, the linker and intercalator connection is defined as the bond between a linker atom and the first atom being part of a conjugated system that is able to co-stack with nucleobases of a strand of a oligonucleotide or oligonucleotide analogue when the oligonucleotide or oligonucleotide analogue is hybridized to an oligonucleotide analogue comprising the intercalator pseudonucleotide.

The linker may comprise a conjugated system and the intercalator may comprise another conjugated system. In this case the linker conjugated system is not capable of co-stacking with nucleobases of the opposite oligonucleotide or oligonucleotide analogue strand.

Linker

The linker of an intercalator pseudonucleotide is a moiety connecting the intercalator and the backbone monomer of the intercalator pseudonucleotide. The linker may comprise one or more atom(s) or bond(s) between atoms.

By the definitions of backbone and intercalator moieties defined herein, the linker is the shortest path linking the backbone and the intercalator. If the intercalator is linked directly to the backbone, the linker is a bond. The linker usually consists of a chain of atoms or a branched chain of atoms. Chains can be saturated as well as unsaturated. The linker may also be a ring structure with or without conjugated bonds. For example, the linker may comprise a chain of m atoms selected from the group consisting of C, O, S, N, P, Se, Si, Ge, Sn and Pb, wherein one end of the chain is connected to the intercalator and the other end of the chain is connected to the backbone monomer unit.

The total length of the linker and the intercalator of the intercalator pseudonucleotides preferably is between 8 and 13 Å. Accordingly, m should be selected dependent on the size of the intercalator of the specific intercalator pseudonucleotide. That is, m should be relatively large, when the intercalator is small and m should be relatively small when the intercalator is large. For most purposes, however, m will be an integer from 1 to 7, such as from 1 to 6, such as from 1 to 5, such as from 1 to 4. As described above, the linker may be an unsaturated chain or another system involving conjugated bonds. For example, the linker may comprise cyclic conjugated structures. Preferably, m is from 1 to 4 when the linker is an saturated chain.

When the intercalator is pyrene, m is preferably an integer from 1 to 7, such as from 1 to 6, such as from 1 to 5, such as from 1 to 4, more preferably from 1 to 4, even more preferably from 1 to 3, most preferably m is 2 or 3.

When the intercalator has the structure

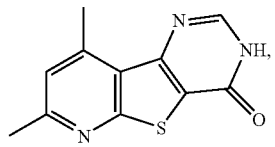

m is preferably from 2 to 6, more preferably 2.

The chain of the linker may be substituted with one or more atoms selected from the group consisting of C, H, O, S, N, P, Se, Si, Ge, Sn and Pb.

In one form, the linker is an azaalkyl, oxaalkyl, thiaalkyl or alkyl chain. For example, the linker may be an alkyl chain substituted with one or more selected from the group consisting C, H, O, S, N, P, Se, Si, Ge, Sn and Pb. In a preferred embodiment the linker consists of an unbranched alkyl chain, wherein one end of the chain is connected to the intercalator and the other end of the chain is connected to the backbone monomer unit and wherein each C is substituted with 2 H. More preferably, the unbranched alkyl chain is from 1 to 5 atoms long, such as from 1 to 4 atoms long, such as from 1 to 3 atoms long, such as from 2 to 3 atoms long.

In another form, the linker is a ring structure comprising atoms selected from the group consisting of C, O, S, N, P, Se, Si, Ge, Sn and Pb. For example the linker may be such a ring structure substituted with one or more selected from the group consisting of C, H, O, S, N, P, Se, Si, Ge, Sn and Pb.

In another form, the linker consists of from 1 to –6 C atoms, from 0 to 3 of each of the following atoms O, S, N. More preferably the linker consists of from 1 to 6 C atoms and from 0 to 1 of each of the atoms O, S, N. In a preferred form, the linker consists of a chain of C, O, S and N atoms, optionally substituted. Preferably the chain should consist of at the most 3 atoms, thus comprising from 0 to 3 atoms selected individually from C, O, S, N, optionally substituted.

In a preferred form, the linker consists of a chain of C, N, S and O atoms, wherein one end of the chain is connected to the intercalator and the other end of the chain is connected to the backbone monomer unit.

The linker constitutes Y in the formula for the intercalator pseudonucleotide X—Y-Q, as defined above, and hence X and Q are not part of the linker.

Preparation of Intercalator Pseudonucleotides

The intercalator pseudonucleotides may be synthesised by any suitable method. One suitable method comprises the steps of a1) providing a compound containing an intercalator comprising at least one essentially flat conjugated system, which is capable of co-stacking with nucleobases of a nucleic acid and optionally a linker part coupled to a reactive group;

b1) providing a linker precursor molecule comprising at least two reactive groups, the two reactive groups may optionally be individually protected; and c1) reacting the intercalator with the linker precursor and thereby obtaining an intercalator-linker;

d1) providing a backbone monomer precursor unit comprising at least two reactive groups, the two reactive groups may optionally be individually protected and/or masked and optionally comprising a linker part; and e1) reacting the intercalator-linker with the backbone monomer precursor and obtaining an intercalator-linker-backbone monomer precursor; or
a2) providing a backbone monomer precursor unit comprising at least two reactive groups, the two reactive groups may optionally be individually protected and/or masked and optionally comprising a linker part;
b2) providing a linker precursor molecule comprising at least two reactive groups, the two reactive groups may optionally be individually protected;
c2) reacting the monomer precursor unit with the linker precursor and thereby obtaining a backbone-linker;
d2) providing a compound containing an intercalator comprising at least one essentially flat conjugated system, which is capable of co-stacking with nucleobases of a nucleic acid and optionally a linker part coupled to a reactive group; and
e2) reacting the intercalator with the backbone-linker and obtaining an intercalator-linker-backbone monomer precursor; or
a3) providing a compound containing an intercalator comprising at least one essentially flat conjugated system, which is capable of co-stacking with nucleobases of a nucleic acid and a linker part coupled to a reactive group;
b3) providing a backbone monomer precursor unit comprising at least two reactive groups, the two reactive groups may optionally be individually protected and/or masked), and a linker part;
c3) reacting the intercalator-linker part with the backbone monomer precursor-linker and obtaining an intercalator-linker-backbone monomer precursor;
f) optionally protecting and/or de-protecting the intercalator-linker-backbone monomer precursor;
g) providing a phosphor containing compound capable of linking two psuedonucleotides, nucleotides and/or nucleotide analogues together;
h) reacting the phosphorous containing compound with the intercalator-linker-backbone monomer precursor; and
i) obtaining an intercalator pseudonucleotide.

Preferably, the intercalator reactive group is selected so that it may react with the linker reactive group. Hence, if the linker reactive group is a nucleophil, then preferably the intercalator reactive group is an electrophile, more preferably an electrophile selected from the group consisting of halo alkyl, mesyloxy alkyl and tosyloxy alkyl. More preferably the intercalator reactive group is chloromethyl. Alternatively, the intercalator reactive group may be a nucleophile group for example a nucleophile group comprising hydroxy, thiol, selam, amine or mixture thereof.

Preferably, the cyclic or non cyclic alkane may be a poly-substituted alkane or alkoxy comprising at least three linker reactive groups. More preferably the poly-substituted alkane may comprise three nucleophilic groups such as, but not limited to, an alkane triole, an aminoalkane diol or mercaptoalkane diol. Preferably the poly-substituted alkane contain one nucleophilic group that is more reactive than the others, alternatively two of the nucleophilic groups may be protected by a protecting group. More preferably the cyclic or non cyclic alkane is 2,2-dimethyl-4-methylhydroxy-1,3-dioxalan, even more preferably the alkane is D-α,β-isopropylidene glycerol.

Preferably, the linker reactive groups should be able to react with the intercalator reactive groups, for example the linker reactive groups may be a nucleophile group for example selected from the group consisting of hydroxy, thiol, selam and amine, preferably a hydroxy group. Alternatively the linker reactive group may be an electrophile group, for example selected from the group consisting of halogen, triflates, mesylates and tosylates. In a preferred form, at least 2 linker reactive groups may be protected by a protecting group.

The method may further comprise a step of attaching a protecting group to one or more reactive groups of the intercalator-precursor monomer. For example a DMT group may be added by providing a DMT coupled to a halogen, such as Cl, and reacting the DMT-Cl with at least one linker reactive group. Accordingly, preferably at least one linker reactive group will be available and one protected. If this step is done prior to reaction with the phosphor comprising agent, then the phosphor comprising agent may only interact with one linker reactive group.

The phosphor comprising agent may for example be a phosphoramidite, for example $NC(CH_2)_2OP(Npr^i_2)_2$ or $NC(CH_2)_2OP(Npr^i_2)Cl$ Preferably the phosphor comprising agent may be reacted with the intercalator-precursor in the presence of a base, such as $N(et)_3$, $N('pr)_2Et$ and $CH_2Cl_2$.

Once the appropriate sequences of oligonucleotide or oligonucleotide analogue are determined, they are preferably chemically synthesised using commercially available methods and equipment. For example, the solid phase phosphoramiditee method can be used to produce short oligonucleotide or oligonucleotide analogue comprising one or more intercalator pseudonucleotides to from an INA.

For example the oligonucleotides or oligonucleotide analogues may be synthesised by any of the methods described in "Current Protocols in Nucleic acid Chemistry" Volume 1, Beaucage et al., Wiley.

INAs—Oligonucleotides Comprising Intercalator Pseudonucleotides

High affinity of synthetic nucleic acids towards target nucleic acids may greatly facilitate detection assays and furthermore synthetic nucleic acids with high affinity towards target nucleic acids may be useful for a number of other purposes, such as gene targeting and purification of nucleic acids. Oligonucleotides or oligonucleotide analogues comprising intercalators have been shown to increase affinity for homologous complementary nucleic acids.

Oligonucleotides or oligonucleotide analogues comprising at least one intercalator pseudonucleotide can be made wherein the melting temperature of a hybrid consisting of the oligonucleotides or oligonucleotide analogues and a homologous complementary DNA (DNA hybrid) is significantly higher than the melting temperature of a hybrid between an oligonucleotide or oligonucleotide analogue lacking intercalator pseudonucleotide(s) consisting of the same nucleotide sequence as the oligonucleotide or oligonucleotide analogue and the homologous complementary DNA (corresponding DNA hybrid).

Preferably, the melting temperature of the DNA hybrid is from 1 to 80° C., more preferably at least 2° C., even more preferably at least 5° C., yet more preferably at least 10° C. higher than the melting temperature of the corresponding DNA hybrid.

Oligonucleotides or oligonucleotide analogues can have at least one internal intercalator pseudonucleotide. Positioning intercalator units internally allows for greater flexibility in design. Nucleic acid analogues comprising internally positioned intercalator pseudonucleotides may thus have higher affinity for homologous complementary nucleic acids than nucleic acid analogues that do- not have internally positioned intercalator pseudonucleotides. Oligonucleotides or oligonucleotide analogues comprising at least one internal intercalator pseudonucleotide may also be able to discriminate between RNA (including RNA-like nucleic acid analogues)

and DNA (including DNA-like nucleic acid analogues). Furthermore internally positioned fluorescent intercalator monomers could find use in diagnostic tools.

The intercalator pseudonucleotides may be placed in any desirable position within a given oligonucleotide or oligonucleotide analogue. For example, an intercalator pseudonucleotide may be placed at the end of the oligonucleotide or oligonucleotide analogue or an intercalator pseudonucleotide may be placed in an internal position within the oligonucleotide or oligonucleotide analogue.

When the oligonucleotide or oligonucleotide analogue comprise more than 1 intercalator pseudonucleotide, the intercalator pseudonucleotides may be placed in any position in relation to each other. For example they may be placed next to each other, or they may be positioned so that 1, such as 2, for example 3, such as 4, for example 5, such as more than 5 nucleotides are separating the intercalator pseudonucleotides. In one preferred embodiment two intercalator pseudonucleotides within an oligonucleotide or oligonucleotide analogue are placed as next nearest neighbours, i.e. they can be placed at any position within the oligonucleotide or oligonucleotide analogue and having 1 nucleotide separating the two intercalator pseudonucleotides. In another preferred form, two intercalators are placed at or in close proximity to each end respectively of the oligonucleotide or oligonucleotide analogue.

The oligonucleotides or oligonucleotide analogues may comprise any kind of nucleotides and/or nucleotide analogues, such as the nucleotides and/or nucleotide analogues described herein above. For example, the oligonucleotides or oligonucleotide analogues may comprise nucleotides and/or nucleotide analogues comprised within DNA, RNA, LNA, PNA, ANA INA, and HNA. Accordingly, the oligonucleotides or oligonucleotide analogue may comprise one or more selected from the group consisting of subunits of PNA, Homo-DNA, b-D-Altropyranosyl-NA, b-D-Glucopyranosyl-NA, b-D-Allopyranusyl-NA, HNA, MNA, ANA, LNA, CNA, CeNA, TNA, (2'-NH)-TNA, (3'-NH)-TNA, α-L-Ribo-LNA, α-L-Xylo-LNA, α-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, α-D-Ribopyranosyl-NA, α-L-Lyxopyranosyl-NA, 2'-R-RNA, 2'-OR-RNA, α-L-RNA, α-D-RNA, β-D-RNA, i.e. the oligonucleotide analogue may be selected from the group of PNA, Homo-DNA, b-D-Altropyranosyl-NA, b-D-Glucopyranosyl-NA, b-D-Allopyranusyl-NA, HNA, MNA, ANA, LNA, CNA, CeNA, TNA, (2'-NH)-TNA, (3'-NH)-TNA, α-L-Ribo-LNA, α-L-Xylo-LNA, α-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, α-D-Ribopyranosyl-NA, α-L-Lyxopyranosyl-NA, 2'-R-RNA, 2'-OR-RNA, α-L-RNA, β-D-RNA, β-D-RNA and mixtures thereof.

One advantage of the oligonucleotides or oligonucleotide analogues is that the melting temperature of a hybrid consisting of an oligonucleotide or oligonucleotide analogue comprising at least one intercalator pseudonucleotide and an essentially complementary DNA (DNA hybrid) is significantly higher than the melting temperature of a duplex consisting of the essentially complementary DNA and a DNA complementary thereto.

Accordingly, oligonucleotides or oligonucleotide analogues may form hybrids with DNA with higher affinity than naturally occurring nucleic acids. The melting temperature is preferably increased with 2 to 30° C., for example from 5 to 20° C., such as from 10° C. to 15° C., for example from 2° C. to 5° C., such as from 5° C. to 10° C., such as from 15° C. to 20° C., for example from 20° C. to 25° C., such as from 25° C. to 30° C., for example from 30° C. to 35° C., such as from 35° C. to 40° C., for example from 40° C. to 45° C., such as from 45° C. to 50° C. higher.

In particular, the increase in melting temperature may be achieved due to intercalation of the intercalator, because the intercalation may stabilise a DNA duplex. Accordingly, it is preferred that the intercalator is capable of intercalator between nucleobases of DNA. Preferably, the intercalator pseudonucleotides are placed as bulge insertions or end insertions in the duplex (see below), which in some nucleic acids or nucleic acid analogues may allow for intercalation.

The melting temperature of an oligonucleotide or oligonucleotide analogue comprising at least one intercalator pseudonucleotide and an essentially complementary RNA (RNA hybrid) or a RNA-like nucleic acid analogue (RNA-like hybrid) can be significantly higher than the melting temperature of a duplex consisting of the essentially complementary RNA or RNA-like target and the oligonucleotide analogue comprising no intercalator pseudonucleotides. Preferably most or all of the intercalator pseudonucleotides of the oligonucleotide or oligonucleotide analogue are positioned at either or both ends.

Accordingly, oligonucleotides and/or oligonucleotide analogues may form hybrids with RNA or RNA-like nucleic acid analogues or RNA-like oligonucleotide analogues with higher affinity than naturally occurring nucleic acids. The melting temperature is preferably increased with from 2 to 20° C., for example from 5 to 15° C., such as from 10° C. to 15° C., for example from 2° C. to 5° C., such as from 5° C. to 10° C., such as from 15° C. to 20° C. or higher.

The intercalator pseudonucleotides will preferably only stabilise towards RNA and RNA-like targets when positioned at the end of the oligonucleotide or oligonucleotide analogue. This does not however exclude the positioning of intercalator pseudonucleotides in oligonucleotides or oligonucleotide analogues to be hybridized with RNA or RNA-like nucleic acid analogues such that the intercalator pseudonucleotides are placed in regions internal to the formed hybrid. This may be done to obtain certain hybrid instabilities or to affect the overall 2D or 3D structure of both intra- and inter-molecular complexes to be formed subsequent to hybridisation.

An oligonucleotide and/or oligonucleotide analogue comprising one or more intercalator pseudonucleotides may form a triple stranded structure (triplex-structure) consisting of the oligonucleotide and/or oligonucleotide analogue bound by Hoogsteen base pairing to a homologous complementary nucleic acid or nucleic acid analogue or oligonucleotide or oligonucleotide analogue. The oligonucleotide or oligonucleotide analogue may increase the melting temperature of the Hoogsteen base pairing in the triplex-structure.

The oligonucleotide or oligonucleotide analogue may increase the melting temperature of the Hoogsteen base pairing in the triplex-structure in a manner not dependent on the presence of specific sequence restraints like purine-rich/pyrimidine-rich nucleic acid or nucleic acid analogue duplex target sequences. Accordingly, the Hoogsteen base pairing in the triplex-structure has significantly higher melting temperature than the melting temperature of the Hoogsteen base pairing to the duplex target if the oligonucleotide or oligonucleotide analogue had no intercalator pseudonucleotides.

Accordingly, oligonucleotides or oligonucleotide analogues may form triplex-structures with homologous complementary nucleic acid or nucleic acid analogue or oligonucleotide or oligonucleotide analogue with higher affinity than naturally occurring nucleic acids. The melting temperature is preferably increased with from 2 to 50° C., such as from 2 to 40° C., such as from 2 to 30° C., for example from 5 to 20° C., such as from 10° C. to 15° C., for example from 2° C. to 5° C., such as from 5° C. to 10° C., for example from 10° C. to 15° C., such as from 15° C. to 20° C., for example from 20° C. to 25° C., such as from 25° C. to 30° C., for example from 30° C. to 35° C., such as from 35° C. to 40° C., for example from 40° C. to 45° C., such as from 45° C. to 50° C.

In particular, the increase in melting temperature may be achieved due to intercalation of the intercalator, because the intercalation may stabilise a DNA triplex. Accordingly, it is preferred that the intercalator is capable of intercalator between nucleobases of a triplex-structure. Preferably, the intercalator pseudonucleotide is placed as a bulge insertion in the duplex (see below), which in some nucleic acids or nucleic acid analogues may allow for intercalation.

Triplex-formation may or may not proceed in strand invasion, a process where the Hoogsteen base-paired third strand invades the target duplex and displaces part or all of the identical strand to form Watson-Crick base pairs with the complementary strand. This can be exploited for several purposes. The oligonucleotides and oligonucleotides are suitably used if only double stranded nucleic acid or nucleic acid analogue target is present and it is not possible, feasible or wanted to separate the target strands, detection by single strand invasion of the region or double strand invasion of complementary regions, without prior melting of double stranded nucleic acid or nucleic acid analogue target, for triplex-formation and/or strand invasion. Accordingly, an oligonucleotide or oligonucleotide analogue comprising at least one intercalator pseudonucleotide is provided that is able to invade a double stranded region of a nucleic acid or nucleic acid analogue molecule.

An oligonucleotide or oligonucleotide analogue comprising at least one intercalator pseudonucleotide that is able to invade a double stranded nucleic acid or nucleic acid analogue in a sequence specific manner can be provided. Invading oligonucleotide and/or oligonucleotide analogue comprising at least one intercalator pseudonucleotide will bind to the complementary strand in a sequence specific manner with higher affinity than the strand displaced.

The melting temperature of a hybrid consisting of an oligonucleotide analogue comprising at least one intercalator pseudonucleotide and a homologous complementary DNA (DNA hybrid), is usually significantly higher than the melting temperature of a hybrid consisting of the oligonucleotide or oligonucleotide analogue and a homologous complementary RNA (RNA hybrid) or RNA-like nucleic acid analogue target or RNA-like oligonucleotide analogue target. The oligonucleotide may be any of the above described oligonucleotide analogues. Accordingly, the oligonucleotides or oligonucleotide analogue may comprise one or more selected from the group consisting of subunits of PNA, Homo-DNA, b-D-Altropyranosyl-NA, b-D-Glucopyranosyl-NA, b-D-Allopyranusyl-NA, HNA, MNA, ANA, LNA, CNA, CeNA, TNA, (2'-NH)-TNA, (3'-NH)-TNA, α-L-Ribo-LNA, α-L-Xylo-LNA, α-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, α-D-Ribopyranosyl-NA, α-L-Lyxopyranosyl-NA, 2'-R-RNA, 2'-OR-RNA, α-L-RNA, α-D-RNA, β-D-RNA, i.e. the oligonucleotide analogue may be selected from the group of PNA, Homo-DNA, b-D-Altropyranosyl-NA, b-D-Glucopyranosyl-NA, b-D-Allopyranusyl-NA, HNA, MNA, ANA, LNA, CNA, CeNA, TNA, (2'-NH)-TNA, (3'-NH)-TNA, α-L-Ribo-LNA, α-L-Xylo-LNA, α-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, α-D-Ribopyranosyl-NA, α-L-Lyxopyranosyl-NA, 2'-R-RNA, 2'-OR-RNA, α-L-RNA, α-D-RNA, β-D-RNA and mixtures thereof comprising at least one intercalator pseudonucleotide.

Accordingly, the affinity of the oligonucleotide or oligonucleotide analogue for DNA is significantly higher than the affinity of the oligonucleotide or oligonucleotide analogue for RNA or an RNA-like target. Hence in a mixture comprising a limiting number of the oligonucleotide or oligonucleotide analogue and a homologous complementary DNA and a homologous complementary RNA or homologous complementary RNA-like target, the oligonucleotide or oligonucleotide analogue will preferably hybridize to the homologous complementary DNA.

Preferably, the melting temperature of the DNA hybrid is at least 2° C., such as at least 5° C., for example at least 10° C., such as at least 15° C., for example at least 20° C., such as at least 25° C., for example at least 30° C., such as at least 35° C., for example at least 40° C., such as from 2 to 30° C., for example from 5 to 20° C., such as from 10° C. to 15° C., for example from 2° C. to 5° C., such as from 5° C. to 10° C., for example from 10° C. to 15° C., such as from 15° C. to 20° C., for example from 20° C. to 25° C., such as from 25° C. to 30° C., for example from 30° C. to 35° C., such as from 35° C. to 40° C., for example from 40° C. to 45° C., such as from 45° C. to 50° C., for example from 50° C. to 55° C., such as from 55° C. to 60° C. higher than the melting temperature of a homologous complementary RNA or RNA-like hybrid.

An oligonucleotide or oligonucleotide analogue containing at least one intercalator pseudonucleotide can be hybridized to secondary structures of nucleic acids or nucleic acid analogues. The oligonucleotide or oligonucleotide analogue is capable of stabilizing such a hybridization to the secondary structure. Secondary structures could be, but are not limited to, stem-loop structures, Faraday junctions, fold-backs, H-knots, and bulges. The secondary structure can be a stem-loop structure of RNA, where an oligonucleotide or oligonucleotide analogue comprising at least one intercalator pseudonucleotide is designed in a way so the intercalator pseudonucleotide is hybridizing at the end of one of the three duplexes formed in the three-way junction between the secondary structure and the oligonucleotide or oligonucleotide analogue.

Position of Intercalator Pseudonucleotide

An oligonucleotide or oligonucleotide analogue can be designed in a manner so it may hybridize to a homologous complementary nucleic acid or nucleic acid analogue (target nucleic acid). Preferably, the oligonucleotide or oligonucleotide analogue may be substantially complementary to the target nucleic acid. More preferably, at least one intercalator pseudonucleotide is positioned so that when the oligonucleotide analogue is hybridized with the target nucleic acid, the intercalator pseudonucleotide is positioned as a bulge insertion, i.e. the upstream neighbouring nucleotide of the intercalator pseudonucleotide and the downstream neighbouring nucleotide of the intercalator pseudonucleotide are hybridized to neighbouring nucleotides in the target nucleic acid.

An intercalator pseudonucleotide can be positioned next to either or both ends of a duplex formed between the oligonucleotide analogue comprising the intercalatorr pseudonucleotide and its target nucleotide or nucleotide analogue, for example the intercalator pseudonucleotide may be positioned as a dangling, co-stacking end.

Intercalator pseudonucleotides can be positioned so that when the oligonucleotide analogue is hybridized with the target nucleic acid, all intercalator pseudonucleotides are positioned as bulge insertions and/or as dangling, co-stacking ends.

Examples of INAs (oligonucleotides containing intercalator pseudonucleotides) are depicted below:

$N_1\text{-}(y)_q\text{-}N_2.$ $N_1\text{-}(y\text{-}N_3)_q\text{---}N_2.$ $(y)_q\text{-}N_2.$ $N_1\text{-}(y)_q.$ $(P)_q\text{---}N_2\text{-}(y)_r,$ $N_1\text{-}(y)_q\text{-}N_2.$ $N_1\text{-}(y\text{-}N_3)_q\text{---}N_2\text{-}(y\text{-}N_3)_r\text{---}N_4.$ wherein $N_1$, $N_2$, $N_3$, $N_4$ individually denotes a sequence of nucleotides and/or nucleotides analogues of at least one nucleotide, y denotes an intercalator pseudonucleotide, and q and r are individually selected from an integer of from 1 to 10.

Intercalating Nucleic Acid (INA)

Intercalating nucleic acids (INAs) are non-naturally occurring polynucleotides containing one or more intercalator pseudonucleotides (IPNs) which can hybridize to nucleic acids (DNA and RNA) with sequence specificity. INAs are candidates as alternatives/substitutes to nucleic acid probes in probe-based hybridization assays because they exhibit several desirable properties. INAs are polymers which hybridize to nucleic acids to form hybrids which are more thermodynamically stable than a corresponding nucleic acid/nucleic acid complex. They are not substrates for the enzymes which are known to degrade peptides or nucleic acids. Therefore, INAs should be more stable in biological samples, as well as, have a longer shelf-life than naturally occurring nucleic acid fragments. Unlike nucleic acid hybridization which is very dependent on ionic strength, the hybridization of an INA with a nucleic acid is fairly independent of ionic strength and is favoured at low ionic strength under conditions which strongly disfavour the hybridization of nucleic acid to nucleic acid. The binding strength of INA is dependent on the number of intercalator groups engineered into the molecule as well as the usual interactions from hydrogen bonding between bases stacked in a specific fashion in a double stranded structure. Sequence discrimination is more efficient for INA recognizing DNA than for DNA recognizing DNA.

INAs are synthesized by adaptation of standard oligonucleotide synthesis procedures in a format which is commercially available.

There are indeed many differences between INA probes and standard nucleic acid probes. These differences can be conveniently broken down into biological, structural, and physico-chemical differences. As discussed above and below, these biological, structural, and physico-chemical differences may lead to unpredictable results when attempting to use INA probes in applications were nucleic acids have typically been employed. This non-equivalency of differing compositions is often observed in the chemical arts.

With regard to biological differences, nucleic acids are biological materials that play a central role in the life of living species as agents of genetic transmission and expression. Their in vivo properties are fairly well understood. INA, however, is a recently developed totally artificial molecule, conceived in the minds of chemists and made using synthetic organic chemistry. It has no known biological function.

Structurally, INA also differs dramatically from nucleic acids. Although both can employ common nucleobases (A, C, G, T, and U), the composition of these molecules is structurally diverse. The backbones of RNA, DNA and INA are composed of repeating phosphodiester ribose and 2-deoxyribose units. INAs differ from DNA or RNA in having one or more large flat molecules attached via a linker molecule(s) to the polymer. The flat molecules intercalate between bases in the complementary DNA stand opposite the INA in a double stranded structure.

The physico/chemical differences between INA and DNA or RNA are also substantial. INA binds to complementary DNA more rapidly than nucleic acid probes bind to the same target sequence. Unlike DNA or RNA fragments, INAs bind poorly to RNA unless the intercalator groups are located in terminal positions. Because of the strong interactions between the intercalator groups and bases on the complementary DNA strand, the stability of the INA/DNA complex is higher than that of an analogous DNA/DNA or RNA/DNA complex.

Unlike other DNA such as DNA or RNA fragments or PNAs, INAs do not exhibit self aggregation or binding properties.

In summary, as INAs hybridize to nucleic acids with sequence specificity, INAs are useful candidates for developing probe-based assays and are particularly adapted for kits and screening assays. INA probes, however, are not the equivalent of nucleic acid probes. Consequently, any method, kits or compositions which could improve the specificity, sensitivity and reliability of probe-based assays would be useful in the detection, analysis and quantitation of DNA containing samples. INAs have the necessary properties for this purpose.

An example of an IPN used for the examples in the present invention was the phosphoramidite of (S)-1-O-(4,4'-dimethoxytriphenylmethyl)-3-O-(1-pyrenylmethyl)-glycerol. It will be appreciated, however, that other chemical forms of IPNs can also be used.

One advantage of oligonucleotides or oligonucleotide analogues containing one or more intercalator pseudonucleotides is that the melting temperature of a hybrid of an homologously complementary DNA (DNA hybrid) and a complementary INA is significantly higher than the melting temperature of a duplex consisting of the homologously complementary DNA and a DNA complementary thereto.

Intercalator Pseudonucleotide (IPN) and Intercalating Nucleic Acid (INA)

By INA is meant an intercalating nucleic acid in accordance with the teaching of WO 03/051901, WO 03/052132, WO 03/052133 and WO 03/052134 (Unest A/S) incorporated herein by reference. An INA is an oligonucleotide or oligonucleotide analogue comprising one or more intercalator pseudonucleotide (IPN) molecules.

INAs have a very high affinity for complementary DNA with stabalisations of up to 10 degrees for internally placed IPNs and up to 11 degrees for end position IPNs. The INA itself is a selective molecule that prefers to hybridise with DNA over complementary RNA. It has been shown that INA's bind 25 times less efficiently to RNA than oligonucleotide primers. Whereas, conventional oligonucleotides, oligonucleotide analogues and PNAs have an equal affinity for both RNA and DNA. Thus INAs are the first truly selective DNA binding agents. In addition, INAs have a higher specificity and affinity for complementary DNA that other natural DNA molecules.

In addition, IPNs stabilise DNA best in AT-rich surroundings which make them especially useful in the field of methylomics research for the amplification of bisulphite treated genomic DNA. This is due to the fact that after bisulphite conversion all unmethylated cytosine bases are converted to uracil and subsequently to thymine after amplification. This results in essentially an AT rich genome ideal for the use of INAs. The IPN is essentially a planar (hetero)polyaromatic compound that is capable of co-stacking with nucleobases in a nucleic acid duplex.

The INA molecule has also been shown to be resistant to exonuclease attack. This makes these molecules especially useful as primers for amplification using enzymes such as phi29 which has inherent exonuclease activity. Thus INA primers used as templates for amplification can be specially modified at their 3' terminus to contain IPN moieties that prevent enzyme degradation.

The present inventor has found two methods that are equally capable of WGA on HGS bisulphite treated DNA samples. Both methods have been shown to result in the amplification of large >10 kb DNA fragments unlike conventional approaches such as Degenerate Oligonucleotide Primed-PCR. One method utilises an isothermal amplification step, while the second utilises a unique blend of thermostable polymerases capable of amplifying bisulphite treated DNA.

Amplification Methods

One example of an amplification strategy is shown below. However, alteration to specific volumes, buffer composition, primer selection etc can result in a more representative amplification.

I. 1 µl of the DNA sample either denatured or not denatured as required is added to an appropriate volume of sample buffer;
II. For each reaction an appropriate volume of reaction buffer is combined with 0.2 µl of polymerase mix and the material mixed by vortexing. This is then combined with the DNA/sample buffer in a volume of 20-50 µl. The amplification reaction is then left at 30° C. for 4-16 hours;
III. The enzyme is heat denatured at 65° C. for 10 minutes;
IV. The amplified DNA is then stored at −20° C. until required Polymerases The polymerase may be phi29 or a modified version thereof. The polymerase is phi29 polymerase (Dean F B et al (2002), Proc, Natl. Acad. Sci, 99(8), 5261-5266). Phi29 polymerase replication of DNA does not require periodic denaturation of the template DNA to remove the newly replicated strand. This replication step can be carried out at around 30° C. degrees for example and allowed to proceed to completion.

The polymerase cocktail may consist of a 5'-deletion mutant of the Taq polymerase enzyme which also contains a small amount of a high fidelity enzyme to increase the representation size. The use of such an enzyme or enzyme cocktail has been shown to reduce the significant template bias that can be generated with conventional PCR enzymes and also result in a much larger representation of amplified fragments (>50 kb).

The use of such a cocktail also results in better amplification of bisulphite treated DNA than conventional PCR enzymes. The use of this specific polymerase mix with proof reading capacity is the first such mix that has been shown to consistently amplify bisulphite treated DNA.

Whole Genome Amplification (WGA)

Typically an amplification reaction is composed of the following components dependent on requirements.

One µl of bisulphite treated DNA is added to the following components in a 25 µl reaction volume, x1 enzyme reaction buffer, 300 ng of each INA or oligonucleotide primer, 3.5 mM MgSO$_4$, 400 µM of each dNTP and 1-2 unit of the polymerase mixture. The components are then cycled in a hot lid thermal cycler as follows.

| Step 1 | 94° C. | 1 minute | 1 cycle |
|---|---|---|---|
| Step 2 | 94° C. | 1 minute | 50 cycles |
| | 37° C. | 2 minutes | |
| | ramp 0.25° C. per second to 55° C. | | |
| | 55° C. | 4 minutes | |
| | 68° C. | 3 minutes | |
| Step 3 | 68° C. | 10 minutes | 1 cycle |

A typical example of the amplification achieved using the WGA method according to the present invention is shown in FIG. 1. Note that often with the WGA method a smear is also seen in the negative control lane due to the very high degree of amplification that is achieved using this method. Amplification time was around 12 hours.

Multiplex Amplification

Typically an amplification reaction is composed of the following components dependant on requirements.

One µl of bisulphite treated DNA is added to the following components in a 25 µl reaction volume, x1 enzyme reaction buffer, 5-100 ng of each $1^{st}$ round INA or oligonucleotide primer, 1.5-4.0 mM MgSO$_4$, 400 µM of each dNTP and 0.5-2 unit of the polymerase mixture. The components are then cycled in a hot lid thermal cycler as follows. Typically there can be up to 200 individual primer sequences in each amplification reaction.

| Step 1 | 94° C. | 15 minute | 1 cycle |
|---|---|---|---|
| Step 2 | 94° C. | 1 minute | 35 cycles |
| | 50° C. | 3 minutes | |
| | 68° C. | 3 minutes | |
| Step 3 | 68° C. | 10 minutes | 1 cycle |

A second round amplification is then performed on a 1 µl aliquot of the first round amplification that is transferred to a second round reaction tube containing the enzyme reaction mix and appropriate second round primers. Cycling is then performed as above.

Gene Specific Amplification

One µl of bisulphite treated DNA is added to the following components in a 25 µl reaction volume, x1 enzyme reaction buffer, 150 ng of each $1^{st}$ round INA or oligonucleotide primer, 1.5-2 MgSO$_4$, 200 µM of each dNTP and 0.5-1 unit of the polymerase mixture. The components are then cycled in a hot lid thermal cycler as follows:

| Step 1 | 94° C. | 1 minute | 1 cycle |
|---|---|---|---|
| Step 2 | 94° C. | 1 minute | 30 cycles |
| | 50° C. | 1 minute | |
| | 68° C. | 3 minutes | |
| Step 3 | 68° C. | 10 minutes | 1 cycle |

A second round amplification is then performed on a 1 μl aliquot of the first round amplification that is transferred to a second round reaction tube containing the enzyme reaction mix and appropriate second round primers. Cycling is then performed as above.

Results

Traditional bisulphite conversion has been shown to result in the loss of up to 96% of the starting input DNA (2001, Grunau C et al, Nucleic Acids Research, 1:29(13):E65-5). Such a loss would not give rise to a representative genome when used in WGA. To overcome this loss the present applicant has developed a new bisulphite conversion method that results in essentially no loss of starting DNA.

Table 2 shows the amplification efficiency of 6 genomic loci in 6 human tissue samples. As can be seen from the results in Table 2, the HGS bisulphite method produced genome coverage at all six loci in all tissues whereas the conventional approach was very limited in terms of genome coverage. Thus DNA treated by the HGS bisulphite conversion method is amenable to WGA applications whereas the use of conventional bisulphite conversion methods for WGA would result in very little genome coverage.

top and bottom strands are no longer complimentary and the strands are deficient in Cs and are AT enriched. Thus to perform WGA on bisulphite treated DNA at least 2 primer populations have to be added instead of one, to target individual strands of the DNA. In addition, after bisulphite conversion, the DNA essentially exists as a cytosine depleted format where the major bases are A, G and T thus the use of any of the four base, containing primers, denoted N (where N=A, C, G or T) for universal amplification is limited. Therefore for bisulphite treated samples, WGA primers would have to be modified. After bisulphite conversion, the DNA exists in a single stranded format with the two strands no longer complimentary. The top strand will consist by and large of only three bases, A G and T. Thus to prime efficiently on this strand, the WGA primer population would have to contain the bases T, C and A. This population is denoted H, where H=(T, C and A) at any position in the primer. After the $1^{st}$ round of amplification the strand would then be copied by the polymerase into the complementary form which would consist essentially of the bases A, C and T. Thus for exponential amplification of the individual DNA strand a second primer would have to be added consisting of the bases T, G and A at

TABLE 2

Amplification efficiency of HGS bisulphite methodology versus traditional bisulphite amplification Procedures (Clark et al, 1994)

| Tissue | HGS Technology amplification of Gene 1-6 | | | | | | Traditional Bisulphite amplification of Gene 1-6 | | | | | |
|---|---|---|---|---|---|---|---|---|---|---|---|---|
| | 1 | 2 | 3 | 4 | 5 | 6 | 1 | 2 | 3 | 4 | 5 | 6 |
| a | yes | yes | yes | yes | yes | yes | no | no | no | no | no | no |
| b | yes | yes | yes | yes | yes | yes | no | yes | yes | no | no | no |
| c | yes | yes | yes | yes | yes | yes | yes | yes | yes | yes | no | yes |
| d | yes | yes | yes | yes | yes | yes | no | yes | yes | no | no | no |
| e | yes | yes | yes | yes | yes | yes | yes | yes | no | no | yes | yes |
| f | yes | yes | yes | yes | yes | yes | yes | no | no | no | no | no |

Tissue samples of Table 2:
a) LNCaP Prostate cancer cell line DNA
b) MCF-7 Breast cancer cell line DNA
c) HepG2 Liver cancer cell line DNA
d) HeLa cervical cancer cell line DNA
e) T-cells from purified Patient # 1
f) CD34+ cells purified from Patient # 1

Whole Genome Amplification Using phi29

Figure 2:
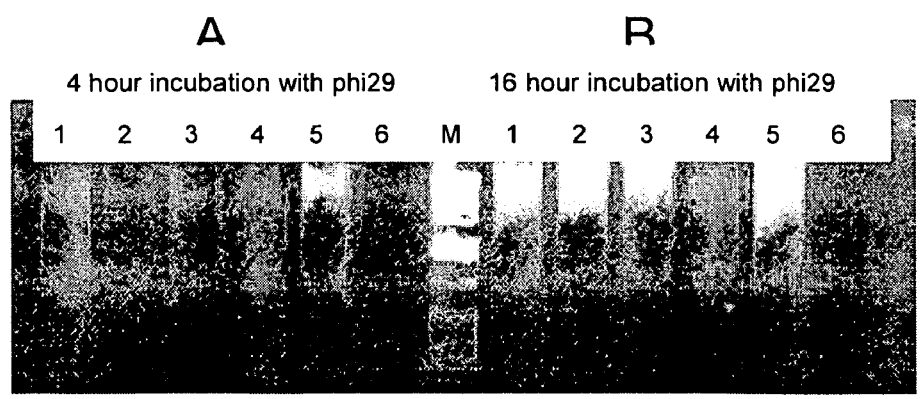
FIG. 2 shows the results of phi29 whole genome bisulphite amplification using HGS bisulphite method. Phi29 amplification of bisulphite treated genomic DNA samples (10 ng). Lane 1: DNA extracted from LNCaP cells, wizard column purified and resuspended in 0.3M NaOH. Lane 2: DNA extracted from LNCaP cells, wizard column purified and resuspended in T/E buffer pH 9. Lane 3: DNA extracted from LNCaP cells, isopropanol precipitated and resuspended in 0.3M NaOH. Lane 4 DNA extracted from LNCaP cells, isopropanol precipitated and resuspended in T/E buffer pH 9. Lane 5: Control LNCaP genomic DNA (not bisulphite treated). Lane 5: Negative control.

A typical example of the amplification achieved using the WGA method according to the present invention with phi29 is shown in FIG. 2. As can be seen from FIG. 2, high molecular weight DNA can be amplified from bisulphite converted DNA. However, the efficiency of amplification was slightly less that with control unconverted DNA as FIG. 2A lane 5 shows that after 4 hour amplification there is more product present in the control genomic DNA that in the bisulphite converted lanes (1-4). However, increasing the time to 16 hours resulted in higher amplification yields of the bisulphite converted DNA (FIG. 2B).

The unique nature of bisulphite modified DNA also means that traditional methods for WGA cannot be applied. This is due to the fact that after bisulphite treatment, the two DNA strands are no longer complementary. For example, a normal DNA 10-mer sequence with a top strand such as 5' GATTGC-CTTC 3' has a complementary bottom strand of 3'CTAACG-GAAG 5'. However, upon bisulphite modification involving the ultimate conversion of Cs to Ts, the top strand becomes 5' GATTGTTTTT 3' and the bottom strand becomes 3' TTAATGGAAG 5'. Owing to this bisulphite conversion, the any position in the primer. This population is denoted D, where D=(T, G and A). FIG. 1 illustrates the problems associated with conventional WGA when the starting template is bisulphite modified DNA. When only one primer population is used for bisulphite WGA, either the D population or the H population, the size of the amplified products (amplicons) is generally limited to <1.5 kb as can be seen in lanes D and H FIG. 1. However, when both D population and H population primers are used together for the WGA of bisulphite treated DNA, then amplification of fragments >20 kb is easily achieved (lane denoted D+H) FIG. 1. Using the traditional WGA approach of X Telenius, H, et al, Genomics, (1992) 13, 718-725, even with modified primers directed against bisulphite treated DNA in which the primers contain H populations, amplicons are again small and are <1.5 kb in size (lanes denoted D+6 and D+7) FIG. 1.

Figure 3:
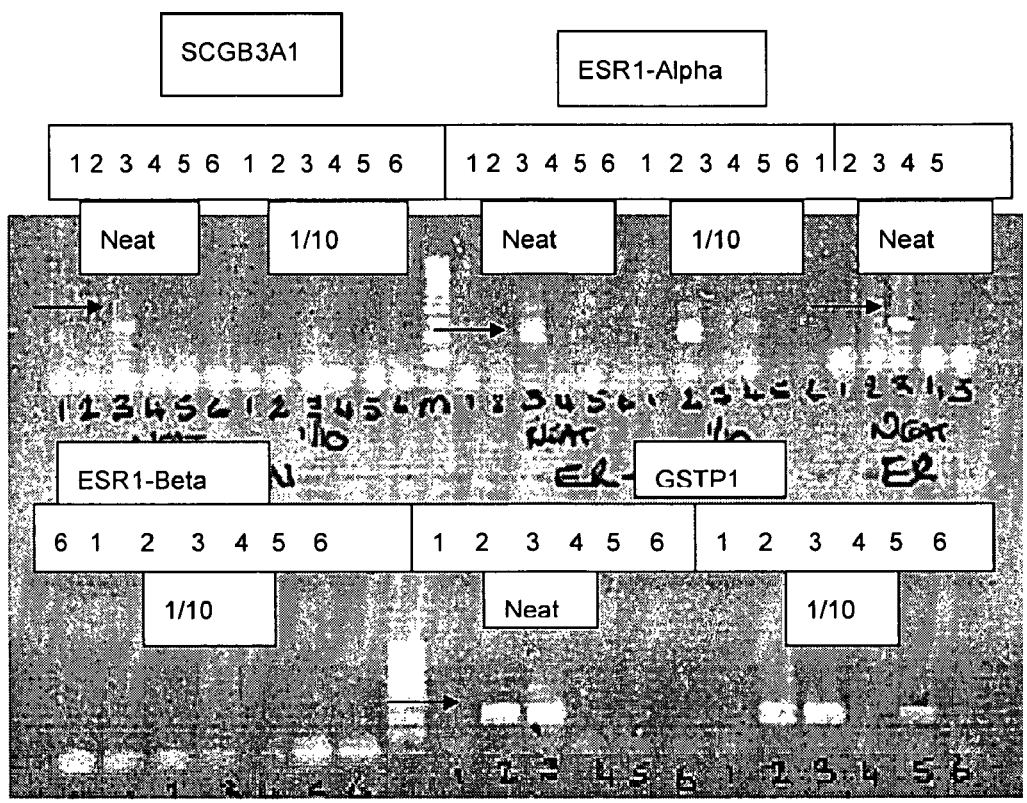
FIG. 3 shows results of whole genome amplification to determine if the genome is randomly amplified as assayed by whether genes selected at random are represented in the WGA mix. Amplification of four genes chosen at random using the WGA samples shown in FIG. 1 using the samples at neat and 1/10 dilutions. DNA obtained from FIG. 1 was used subsequently to amplify the following 4 genomic loci as defined by locuslink; SCGB3A1, ESR1-alpha, ESR1-beta and GSTP1. Lane 1: WGA amplification using D15 population primer only. Lnae 2: WGA amplification using H15 population primer only. Lane 3: WGA amplification using D15 and H15 population primers. Lane 4: WGA amplification using D+6 primer only (TTYGAGHHHHHHMGYGA). Lane 5: WGA amplification using D+6 primer only (TTYG-AGHHHHHHHAAGYGA). Lane 6: Negative control. NB. Primers D+6 and D+7 were based on the primers used by 1992 Telenius. H, et al Genomics, 13, 718-725 but modified to include H population primers instead of N population primers.

To determine the genome coverage obtained using the preferred method according to the present invention, the present inventor subjected the WGA DNA amplified in FIG. 1 to PCR analysis at four independent genomic loci, SCGB3A1, ESR1-alpha, ESR1-beta and GSTP1. If the method successfully amplified bisulphite treated DNA then all genomic loci should be amplified. If there is non randomness in the method, then some genomic loci will not be amplified, and they will not be represented amongst the amplicons. FIG. 3 shows the results of our amplifications. The only WGA method to produce uniform genomic representations was amplified with the D and H primers combinations. No other combination or the use of single primer WGA has produced consistent genomic coverage.

Thus the WGA method with novel bisulphite conversion technology that results in virtually no loss of genomic DNA and modified DNA primers allows the amplification of large fragments of DNA suitable for downstream applications. The use of such approaches has enabled WGA from bisulphite treated DNA from <10 cells thus enabling whole genome analysis to be undertaken from small samples such as archival specimens, laser dissected cell populations, samples from developing human blastocysts and small populations of circulating cancer cells or embryonic stem cell populations.

Whole Genome Amplification Using a Cocktail of Polymerases or a Single Polymerase Alone.

Figure 4:
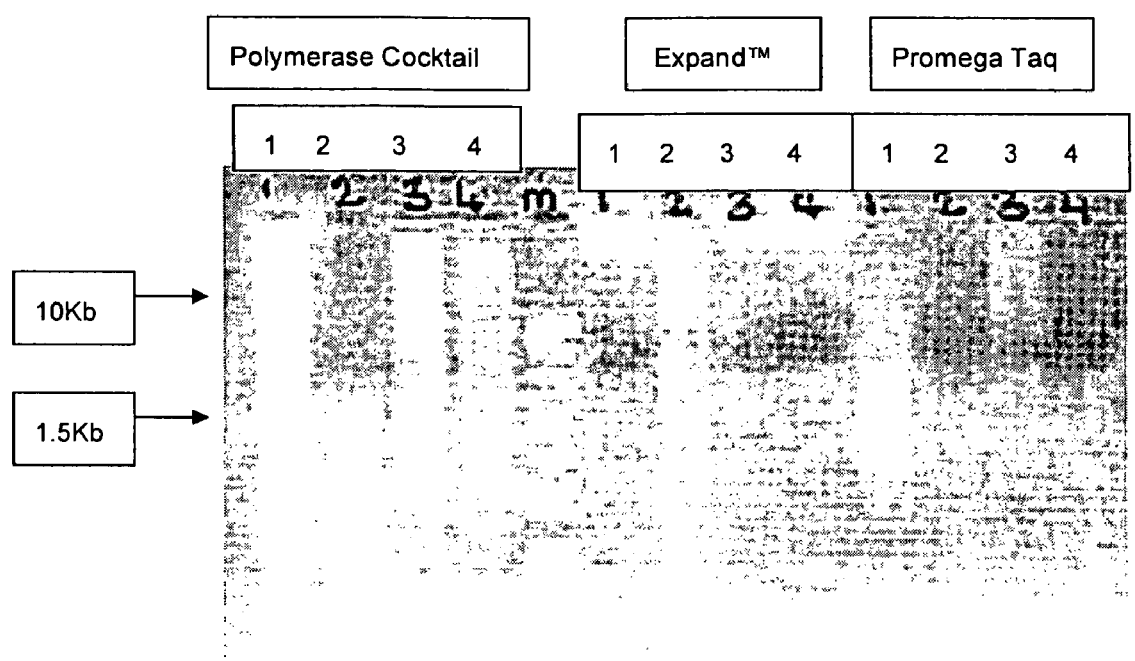
FIG. 4 shows the effect of polymerases on the performance of WGA. Lane 1: WGA amplification using D15 primer and H15 primers. Lane 2: WGA amplification using D15 primer and N15 primers. Lane 3: WGA amplification using H15 primer and N15 primers. Lane 4: No DNA Control. WGA performed using the Taq polymerase deletion mutant cocktail, Expand™ (Roche) and Promega Taq polymerase.

FIG. 4 demonstrates the drawbacks of traditional WGA methods and the advantages of the methodology of the present invention. WGA amplification was attempted using three different strategies, a polymerase cocktail, a proof reading enzyme (Expand™) and a single non-proof reading polymerase. Each strategy employed three different primer combinations, the use of D (T, G and A)+H (T, C and A) primer populations, the use of D+N (T, C, G and A) populations and H+N populations.

When the polymerase cocktail was used in combination with D+H primer populations high molecular weight DNA (>30 kb) was amplified from HGS bisulphite treated DNA (FIG. 4). However, when a proof reading enzyme (Expand™) or a single non-proof reading enzyme was used either no DNA or DNA to around 1.5 kb was amplified (FIG. 4). The use of other primer combinations such as D+N or H+N resulted in significantly less or no amplification of the HGS bisulphite treated DNA.

To confirm that genomic representations were achieved the DNA amplified was then PCR amplified using 4 independent genomic loci. The only WGA method that gave rise to representative genomic coverage was the DNA amplified from the polymerase cocktail using the D+H primer combination.

Thus the WGA method according to the present invention reliably produced high molecular weight genomic representations suitable for further downstream applications.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for whole genome amplification comprising:
    (a) treating genomic DNA with a bisulphite reagent to form treated genomic DNA, removing the bisulphite reagent and incubating the treated genomic DNA at pH of between 10 and less than 12.5 to form substantially unfragmented single stranded modified DNA, wherein cytosine bases but not 5'-methyl-cytosine bases in the genomic DNA are modified to uracil bases to form the modified DNA;
    (b) providing a population of random X-mers of exonuclease-resistant primers capable of binding to at least one strand of the modified DNA, wherein X is an integer 3 or greater, and wherein the primers are formed of two populations of primers, the first population comprising random X-mers containing only the bases A, G and T, and the second population comprising random X-mers containing only the bases A, C and T;
    (c) contacting the modified DNA and the population of random X-mers with nucleotides and a polymerase capable of amplifying double stranded DNA; and
    (d) allowing the polymerase to amplify the modified DNA.

2. The method according to claim 1 wherein the bisulphite reagent is sodium bisulphite.

3. The method according to claim 1 wherein the exonuclease-resistant primers are oligonucleotides or oligonucleotide analogues containing at least one intercalator pseudo-nucleotide forming an intercalating nucleic acid (INA).

4. The method according to claim 3 wherein the oligonucleotide or oligonucleotide analogue is selected from the group consisting of subunits of DNA, RNA, peptide nucleic acid (PNA), hexitol nucleic acid (HNA), MNA, altritol nucleic acid (ANA), locked nucleic acid (LNA), cyclohexanyl nucleic acid (CAN), CeNA, TNA, (2'-NH)-TNA, nucleic acid based conjugates, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo [4.3.0]-DNA, Bicyclo [3.2.1]-DNA, Bicyclo [4.3.0]amide-DNA, β-D-Ribopyranosyl-NA, α-L-Lyxopyranosyl-NA, 2'-R-RNA, 2'-OR-RNA, α-L-RNA, and β-D-RNA.

5. The method according to claim 1 wherein the exonuclease-resistant primers are intercalating nucleic acids (INAs) formed from oligonucleotides.

6. The method according to claim 1 wherein the primers are formed of two populations of INA primers, the first population being random X-mers containing only the bases A, G and T, and the second population comprising random X-mers containing only the bases A, C and T.

7. The method according to claim 6 wherein one population of primers is capable of binding to one strand of DNA while the other population of primers is capable of binding to a complimentary synthesized strand of the DNA stand to which the first population of primers bind.

8. The method according to claim 7 wherein the primers contain from 3 to 40 bases.

9. The method according to claim 8 wherein the primers contain about 6 to 20 bases.

10. The method according to claim 1 wherein the polymerase is phi29, a modified version thereof, or a functional equivalent thereof capable of amplifying double stranded DNA in vitro without the need to denature the DNA.

11. The method according to claim 10 wherein the polymerase is phi29.

12. The method according to claim 1 wherein the polymerase comprises a polymerase cocktail comprising a mixture of at least one proof-reading DNA polymerase and at least one non proof-reading DNA polymerase, wherein the ratio of proof-reading polymerase to non proof-reading polymerase is at least about 1:2.

13. The method according to claim 12 wherein the proof-reading DNA polymerase is selected from the group consisting of Pfu polymerase, Pfu polymerase turbo, Vent polymerase, Vent exo- polymerase, Pwo polymerase, 9°N$_m$DNA polymerase, Therminator, Pfx DNA polymerase, Expand DNA polymerase, rTth DNA polymerase, and DyNAzyme EXT Polymerase.

14. The method according to claim 12 wherein the non proof-reading DNA polymerase is selected from the group consisting of Taq polymerase, Taq polymerase Stoffel fragment, Advantage DNA polymerase, AmpliTaq, Amplitaq Gold, Titanium Taq polymerase, KlenTaq DNA polymerase, Platinum Taq polymerase, and Accuprime Taq polymerase.

15. The method according to claim 12 wherein the ratio of proof-reading polymerase to non-proof-reading polymerase is at least about 1:5.

16. The method according to claim 15, wherein the ratio of proof-reading polymerase to non-proof-reading polymerase about 1:10.

17. The method according to claim 12 wherein step (d) is carried out by DNA thermal cycling.

18. The method according to claim 1 wherein cytosine methylation of the genomic DNA is determined from the amplified DNA.

19. The method according to claim 1 wherein the bisulphite reagent is sodium metabisulphite.

20. The method according to claim 1 wherein the treated genomic DNA is incubated at about 37° C. to about 96° C.

21. The method according to claim 1 wherein the treated genomic DNA is incubated for 2 minutes to 96 hours.

22. The method according to claim 1 wherein the treated genomic DNA is incubated at pH 10.5.

* * * * *